US007879799B2

(12) United States Patent
Martin et al.

(10) Patent No.: US 7,879,799 B2
(45) Date of Patent: Feb. 1, 2011

(54) METHODS FOR CHARACTERIZING GLYCOPROTEINS AND GENERATING ANTIBODIES FOR SAME

(75) Inventors: Dan Martin, Seattle, WA (US); Bernd Wollscheid, Zurich (CH); Rudolf H. Aebersold, Zurich (CH); Julian Watts, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 258 days.

(21) Appl. No.: 11/891,487

(22) Filed: Aug. 9, 2007

(65) Prior Publication Data

US 2008/0108152 A1 May 8, 2008

Related U.S. Application Data

(60) Provisional application No. 60/837,254, filed on Aug. 10, 2006, provisional application No. 60/876,883, filed on Dec. 22, 2006, provisional application No. 60/878,753, filed on Jan. 5, 2007.

(51) Int. Cl.
*A61K 38/00* (2006.01)
*C07K 14/00* (2006.01)
(52) U.S. Cl. .......................... 514/8; 530/300
(58) Field of Classification Search ....................... None
See application file for complete search history.

(56) References Cited

U.S. PATENT DOCUMENTS

| 5,714,350 | A | 2/1998 | Co et al. |
| 6,225,047 | B1 | 5/2001 | Hutchens et al. |
| 6,670,194 | B1 | 12/2003 | Aebersold et al. |
| 7,183,118 | B2 | 2/2007 | Aebersold et al. |
| 2001/0049105 | A1 | 12/2001 | Singh |
| 2002/0022233 | A1 | 2/2002 | Wells |
| 2002/0090652 | A1 | 7/2002 | Fu |
| 2002/0137134 | A1 | 9/2002 | Gerngross |
| 2002/0192720 | A1 | 12/2002 | Parker |
| 2003/0044843 | A1 | 3/2003 | Tanaka |
| 2003/0064359 | A1 | 4/2003 | Lanoix |
| 2003/0186889 | A1 | 10/2003 | Forssmann |
| 2003/0219731 | A1 | 11/2003 | Weinberger |
| 2004/0023306 | A1 | 2/2004 | Aebersold |
| 2004/0038307 | A1 | 2/2004 | Lee |
| 2004/0142379 | A1 | 7/2004 | St. Hilaire |
| 2004/0248317 | A1 | 12/2004 | Swamy |
| 2004/0253659 | A1 | 12/2004 | Rasamoelisolo |
| 2005/0054088 | A1 | 3/2005 | Rahbar |
| 2005/0084924 | A1 | 4/2005 | Shults |
| 2005/0095649 | A1 | 5/2005 | Aebersold |
| 2005/0100956 | A1 | 5/2005 | Apffel |
| 2005/0158708 | A1 | 7/2005 | Alroy |
| 2006/0057638 | A1 | 3/2006 | Bosques |
| 2006/0141528 | A1 | 6/2006 | Aebersold |

FOREIGN PATENT DOCUMENTS

| JP | 2004/059477 | 9/2005 |
| WO | WO 03/087821 | 10/2003 |
| WO | WO 03/102018 | 12/2003 |
| WO | WO 2004/019040 | 3/2004 |
| WO | WO 2005/052182 | 6/2005 |
| WO | WO 2005/076013 | 8/2005 |

OTHER PUBLICATIONS

Alix, "Predictive estimation of protein linear epitopes by using the program PEOPLE," *Vaccine* 18:311-314 (1999).
Barlow et al., "Continuous and discontinuous protein antigenic determinants," *Nature*, 322:747-748 (1986).
Blythe and Flower, "Benchmarking B cell epitope prediction: underperformance of existing methods," *Protein Sci.* 14:246-248 (2005).
Desiere et al., "Integration with the human genome of peptide sequences obtained by high-throughput mass spectrometry" *Genome Biol.* 6:R9 (2004).
Doolittle, *Of URFS and ORFS: A Primer on How to Analyze Derived Amino Acid Sequences*, University Science Books, Chapter 5, pp. 63-79 (1986).
Donadio, et al., "Both core and terminal glycosylation alter epitope expression in thyrotropin and introduce discordancies in hormone measurements," *Clin. Chem. Lab Med.* 43:519-530 (2005).
Harlow and Lane, *Antibodies: A Laboratory Manual*, Cold Spring Harbor Laboratory Press (1988).
Larsen et al., "Improved method for predicting linear B-cell epitopes," *Immunome Res.* 2:2 (2006).
Nesvizhskii et al., "A statistical model for identifying proteins by tandem mass spectrometry," *Anal. Chem.* 75:4646-4658 (2003).
Odorico and Pellequer, "BEPITOPE: predicting the location of continuous epitopes and patterns in proteins," *J. Mol. Recognit.* 16:20-22 (2003).
Pellequer et al., "Predicting location of continuous epitopes in proteins from their primary structures," *Methods Enzymol.* 203:176-201 (1991).
Petrescu et al., "Statistical analysis of the protein environment of N-glycosylation sites: implications for occupancy, structure, and folding," *Glycobiology*, 14:103-114 (2004).

(Continued)

*Primary Examiner*—Michail A Belyavskyi
(74) *Attorney, Agent, or Firm*—Morrison & Foerster LLP

(57) ABSTRACT

The invention provides methods for generating an antibody specific for the deglycosylated form of a glycopolypeptide using a peptide corresponding to an N-linked glycosylation site of a glycopolypeptide. The invention additionally provides methods for generating an antibody specific for a glycopolypeptide using a peptide corresponding to amino acids adjacent to an authentic N-linked glycosylation site.

9 Claims, 4 Drawing Sheets
(3 of 4 Drawing Sheet(s) Filed in Color)

OTHER PUBLICATIONS

Schmitz, et al., "Monoclonal antibodies raised against membrane glycoproteins from mouse brain recognize N-linked oligomannosidic glycans," *Glycobiology*, 3:609-617 (1993).

Sollner and Mayer, "Machine learning approaches for prediction of linear B-cell epitopes on proteins," *J. Mol. Recognit.* 19:200-208 (2006).

Tam and Zavala, "Multiple antigen peptide. A novel approach to increase detection sensitivity of synthetic peptides in solid-phase immunoassays" *J. Immunol. Methods* 124:53-61 (1989).

Tam, "Synthetic peptide vaccine design: synthesis and properties of a high-density multiple antigenic peptide system," *Proc. Natl. Acad. Sci.* USA, 85:5409-5413 (1988).

Tao et al., "Quantitative phosphoproteome analysis using a dendrimer conjugation chemistry and tandem mass spectrometry," *Nat. Methods* 2:591-598 (2005).

Von Haller et al., Mass spectrometric characterization of proteins extracted from Jurkat T cell detergent-resistant membrane domains, *Proteomics*, 1:1010-1021 (2001).

Wollscheid et al., "Lipid raft proteins and their identification in T lymphocytes," *Subcell. Biochem.* 37:121-152 (2004).

Wollscheid et al., "Proteomics/genomics and signaling in lymphocytes," *Curr. Opin. Immunol.* 16:337-344 (2004).

Zhang, et al., "Identification and quantification of N-linked glycoproteins using hydrazide chemistry, stable isotope labeling and mass spectrometry," *Nat. Biotechnol.* 21:660-666 (2003).

Zolg and Langen, "How industry is approaching the search for new diagnostic markers and biomarkers," *Mol. Cell. Proteomics* 3:345-354(2004).

FIGURE 3

METHODS FOR CHARACTERIZING GLYCOPROTEINS AND GENERATING ANTIBODIES FOR SAME

This application claims the benefit of priority of U.S. Provisional application Ser. No. 60/837,254, filed Aug. 10, 2006, U.S. Provisional application Ser. No. 60/876,883, filed Dec. 22, 2006, and U.S. Provisional application Ser. No. 60/878,753, filed Jan. 5, 2007, each of which the entire contents are incorporated herein by reference.

This invention was made with government support under grant number RO1-AI-41109-01 awarded by the National Institutes of Health and grant number NO1-HV-28179 awarded by the National Heart, Lung and Blood Institute. The government has certain rights in the invention.

BACKGROUND OF THE INVENTION

The present invention relates generally to the field of proteomics and more specifically to glycoproteins and membrane proteins.

The molecular composition and dynamic organization of the plasma membrane (PM) determines how a cell can interact with its environment at any given moment in time. Proteins embedded in the membrane that have exposed, extracellular domains are crucial for cell-cell communication, interaction with pathogens, binding of chemical messengers, and response to environmental perturbations. In order to distinguish between proteins that localize to intracellular and plasma membrane domains, methods are needed that will allow for the specific identification of the proteins present on the surface of any given cell.

Thus, there exists a need to efficiently identify, characterize and generate reagents for membrane proteins. The present invention satisfies this need and provides related advantages as well.

SUMMARY OF INVENTION

The invention provides methods for generating an antibody specific for the deglycosylated form of a glycopolypeptide using a peptide corresponding to an N-linked glycosylation site of a glycopolypeptide. The invention additionally provides methods for generating an antibody specific for a glycopolypeptide using a peptide corresponding to amino acids adjacent to an authentic N-linked glycosylation site.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows that covalent modification of carbohydrates (A) takes place following oxidation to aldehydes (B), forming a covalent hydrazone bond (C). The biotinylation reagent, biocytin hydrazide (D) contains a long spacer chain and will not cross the plasma membrane.

FIG. 3 shows identified proteins of lipid raft co-isolated proteins before and after applying the cell surface glyco-capture technology. FIG. 3A shows dentified proteins in a membrane preparation without using the cell surface glyco-capture technology. FIG. 3B shows identified proteins in a membrane preparation using the cell surface glyco-capture technology.

DETAILED DESCRIPTION OF THE INVENTION

Figure 1:
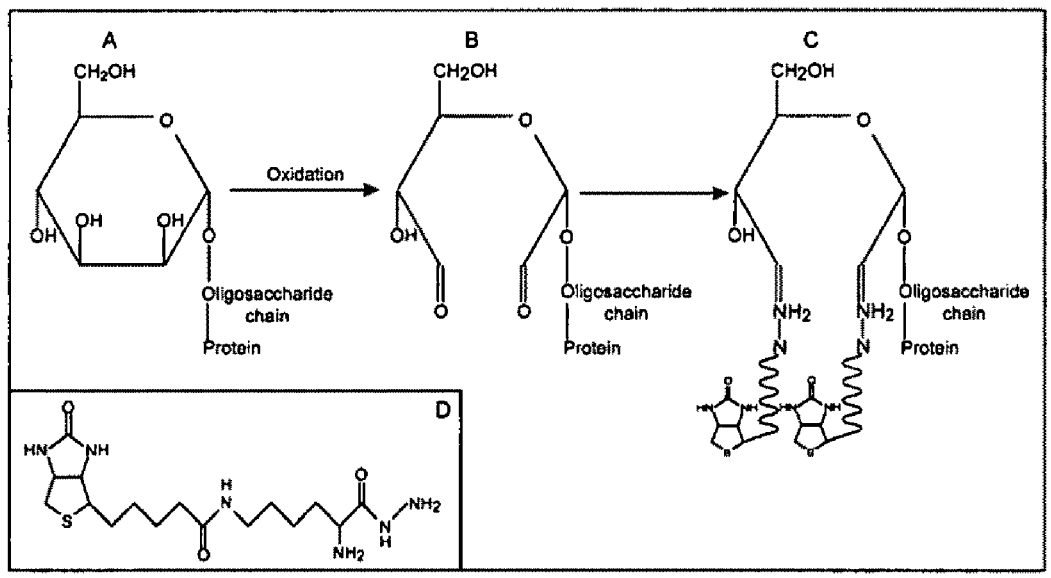
FIG. 1 shows exemplary chemistry for the covalent modification of carbohydrate using the biotinylation reagent biocytin hydrazide.

The present invention relates to efficiently identifying membrane proteins, in particular the extracellular domains of membrane glycoproteins. The invention further relates to reagents such as antibodies that bind to deglycosylated or native forms of a glycoprotein.

Cell surface proteins of human cells can be markers of disease and are potential targets for pharmaceutical intervention. The present invention relates to a technology to selectively identify N-linked cell surface glycoproteins via mass-spectrometry. With this technique, proteins with N-linked carbohydrates that reside only on the extracellular cell membrane at a given time are purified. Because the motifs of glycosylation are known, and because the technique causes a mass shift of one mass unit at the site of carbohydrate attachment, the method reveals the exact site of N-glycosylation within an identified tryptic peptide of a cell surface glycoprotein. Given that carbohydrates are highly hydrated and hydrophilic, the mass spectrometry findings of methods of the invention permit inferences about the structural orientation of the protein in the membrane. Specifically, the results identify regions of the protein sequence that are (1) oriented towards the extracellular environment as opposed to being buried within the hydrophobic core of the protein and (2) located on the outer side of the cell membrane.

The results disclosed herein using methods of the invention have profound implications for research which require specific antibodies against cell surface and secreted proteins. Historically, raising antibodies against human cell surface proteins has been difficult for several reasons. First, there is a high degree of sequence similarity between proteins in different species which causes tolerance to immunization. Second, it is difficult to select immunogenic peptides from cell surface proteins because they are so frequently modified by carbohydrates and other molecular entities that conceal the epitope in the native protein from any antibody generated using a synthetic peptide.

To date, immunizing peptides are chosen according to a combination of theoretical parameters and "common knowledge". Most frequently, a peptide is chosen from the amino or carboxy terminus of the cell surface protein, assuming that this location in the sequence string will make it accessible in the native protein. This algorithm is a crude science; it is usually made without knowledge of the orientation of the protein within the membrane, or by relying on theoretical orientation prediction algorithms. The relative antigenicity of a peptide string can be estimated to some extent by using prediction algorithms, though again, these programs do not take orientation into account.

As disclosed herein, methods are provided for the selection of peptides from cell surface proteins for the generation of antibodies based on the previous MS identification of N-glycosylation sites that should dramatically increase the likelihood of developing a reagent that recognizes the native protein compared to standard methods.

The identification of disease specific biomarkers is one of the major goals of translational research. "Biomarkers" such as prostate specific antigen (PSA), are broadly defined as an assayable characteristic that correlates with a biological process. Protein biomarkers have recently reemerged as prime research targets because (1) they can be sampled easily from body fluids, (2) they are reflective of host physiology, (3) they have demonstrated value as diagnostic agents for a number of clinical conditions, and (4) protein profiling technology and improved proteomics techniques have become feasible. Protein biomarkers in cancer can generally be classified as those that (1) predict the tumor behavior based on the presence or absence of the marker within the tumor sample (local biomarkers) and (2) those that, because of their presence in body fluid, can be used to screen for or monitor disease (disseminated biomarkers). These groups are not necessarily mutually exclusive. The first category of biomarkers includes proteins such as the estrogen receptor and Her-2/neu protein in breast cancer. Pathologic analysis now routinely includes these markers because of their relationship to prognosis and response to therapy. The latter class of biomarkers includes PSA and alpha fetoprotein, which can be used either as a screening test or a marker for disease progression or recurrence (for prostate cancer or germ cell tumor, respectively) (Kolonel et al., *Cancer Epidemiol. Biomarkers Prev.* 9 795-804 (2000)).

The development of new research tools in the last decade has fostered new approaches to identify biomarkers of both classes. Research to identify the local protein biomarkers that can differentiate tumor behavior has been performed in earnest for many years through extensive analysis at both the DNA and protein levels using both cell lines and tumor samples. There have been exciting breakthroughs recently in genomic analysis using array platforms (reviewed in Ntzani and Ioannidis, *The Lancet* 362:1439-1444 (2003)). The field of proteomics has also developed dramatically over the last decade, allowing in-depth study of cancer tissues and cell lines using high-throughput mass spectrometry based techniques (Aebersold and Mann, *Nature,* 422:198-207 (2003); Domon and Aebersold, *Science,* 312:212-217 (2006)). While generating numerous insights into molecular function and systems biology, the translation of specific protein identity into assays with clinical utility has lagged. Interest in biomarkers persists despite limited successes because effective cancer biomarkers could dramatically impact health and research through early disease detection, guiding treatment through "personalized" treatment plans, and enhancing drug development by indicating therapeutic responses. Unfortunately, few new tests based on proteomic or genomic technologies are forthcoming; new drug and biologic submissions to the FDA have dropped over the last decade, despite hopes raised with the human genome project (Anderson and Hunter, *Mol. Cell. Proteomics,* 5:573-588 (2006)).

One of the major reasons for the slow translation of genomic and proteomic insights into new diagnostic assays are the difficulties in generating suitable test platforms. In the case of proteomics, mass spectrometry serves well as a research instrument; however the cost and complexity have limited integration into the clinical realm. In addition, validating clinical biomarkers typically requires sensitive and accurate quantification of candidates in hundreds to thousands of individual samples. The current gold standard of quantitative protein bioassay is the Enzyme-Linked Immunosorbent Assay (ELISA). A good performing ELISA can be run at high-throughput with both extraordinary sensitivity (detection limits ~5 pg/ml) and specificity. Antibody based reagents are also the gold standard in immunohistochemistry, where only a single antibody is required for pathologic analysis of a clinical sample. Such reagents are indispensable in providing certainty for complex medical diagnosis and in tailoring treatment. Numerous examples exist of antibody based reagents. Screening with a PSA ELISA, while somewhat controversial (Harris and Lohr, *Ann. Intern. Med.* 137: 917-929 (2002); *Ann. Intern. Med.* 137:915-916 (2002); Carroll et al., *Urology* 57:217-224 (2001); Smith et al., *CA Cancer J. Clin.* 50:34-49 (2000)), is widely practiced (Routh and Leibovich, *Mayo Clin. Proc.* 80:899-907 (2005)). Antibodies form the basis of numerous other serum assays in the evaluation of malignancy including alpha fetoprotein and βhCG in germ cell tumors and carcinoembryonic antigen (CEA) in colonic neoplasms; antibody based flow cytometry is standard in the diagnosis of hematologic malignancies. Immunotherapy has been demonstrated to be highly efficacious in the treatment of malignancies; Trastuzumab (breast cancer), rituximab (B-cell lymphoma), bevacizumab and cetuximab (Colon cancer), Alemtuzumab (chronic lymphocytic leukemia) are a few examples of agents widely used in clinical oncology (Armitage et al., *Clinical Oncology,* 3rd edition, New York: Churchill Livingstone (2004)). Numerous other antibody based therapeutics are currently under investigation in multiple areas of clinical medicine.

ELISAs are costly to develop (≧$40,000 per biomarker) and have a long development lead-time (>1 year). Much of the difficulties associated with producing new immunologic reagents lie in generating a specific B-cell immune response. To add to this challenge, for clinical tests it is highly desirable to have immunoreactivity proteins in the native state. While some assays such as western blotting do not require such reactivity, it is the sine qua non for flow cytometric cell sorting, pathologic analysis, ELISA analysis, and the like. In addition, in vivo therapeutic assays or methods require antibodies that react with proteins in the native state. Immunization of an animal for the purpose of generating an antibody must provide the host B-cell with an antigen that is unique to the protein of interest and in a state of presentation that is identical to that of the desired target. Most B-cell epitopes are composed of different parts of the polypeptide chain that are brought into spatial proximity by protein folding, which is referred to as "discontinuous" epitopes. It has been estimated that for approximately 10% of epitopes, the corresponding antibodies cross-react with a continuous linear peptide fragment (Pellequer et al., *Methods Enzymol.* 203:176-201 (1991); Barlow et al., *Nature,* 322:747-748 (1986)); such epitopes are denoted linear or continuous epitopes.

Antibodies can be generated through inoculation of whole protein or a peptide epitope. Whole protein is frequently obtained as a recombinant fusion protein produced in bacteria due to the ease of molecular biology required and the abundance of expression and purification systems on the market. Whole protein exposes the host animal to both continuous and discontinuous epitopes. Unfortunately, recombinant proteins are frequently inadequate immunogens; they are often incorrectly folded with misaligned disulfide bonding. In addition, membrane proteins are not easily expressed in bacterial or eukaryotic systems. Post translational modification within the expression system often does not recapitulate that of the original organism; glycosylation is absent in prokaryotic systems and is not guaranteed to be identical in eukaryotic systems, for example, insect cells or yeast cells. Finally, purification frequently generates impure mixtures of proteins, complicating the antibody response following immunization.

A second approach commonly utilized to generate antibodies is to immunize an animal with a continuous peptide sequence from the protein of interest. Small molecules such as peptides are not usually immunogenic, even when co-administered with adjuvants to increase the intensity of the immune response. In order to generate a response to peptide immunogens, they are generally attached to an immunogenic carrier protein, termed a hapten. The most commonly used carrier protein is keyhole limpet hemocyanin (KLH), a mollusk respiratory heme protein. Because KLH shares no homology with vertebrate proteins, antibody responses against the carrier protein results in no cross-reactivity in assays against mammalian proteins. A second option frequently used is the Multiple Antigen Peptide System (MAPS) in which multiple identical peptides linked to a small immunogenically inert branched lysine core (Tam, *Proc. Natl. Acad. Sci. USA.* 85:5409-5413 (1988); Tam and Zavala, *J. Immunol. Methods* 124:53-61 (1989)). This MAP molecule is a larger three dimensional molecule that does not need a carrier protein to induce an antibody response; MAPS peptides avoid generation of antibodies to the commonly used carrier proteins, although they may contain antibodies specific to the MAPS core structure. Altogether peptide immunization is a highly inexact science that depends on both knowledge and chance.

The greatest difficulty in using a continuous peptide antigen is choosing a sequence that produces an antibody to the full length folded protein. Extensive research over the last three decades has produced little progress in predicting linear B-cell epitopes. The classical methods employed use a variety of propensity scales to assign a numerical value to every amino acid based on studies of their physico-chemical properties. These algorithms then apply a running average window to generate a local average score. The first score was that of Hopp and Woods (Hopp, *Pept. Res.* 6:183-190 (1993); Hopp and Woods, *Proc. Natl. Acad. Sci. USA* 78:3824-3828 (1981)), who developed a scale of hydrophilicity. Kyte and Doolitle proposed a similar method based on a separate scale of hydrophobicity (Kyte and Doolittle, *J. Mol. Biol.* 157:105-132 (1982)). A scale of peptide flexibility was first introduced by Karplus (Karplus and Schultz, *Naturwissenschaften* 72:212-213 (1985)); a surface accessibility scale was also introduced (Emini et al., *J. Virol.* 55:836-839 (1985)). It has been shown that protein regions corresponding to the antigenic peptides are usually highly mobile (Westhof et al., *Nature* 311:123-126 (1984); Tainer et al., *Nature,* 312:127-134 (1984)). The number of available scales has grown to over 500 since the 1980's; most are subtle variants on those described above. Most of the propensity scales were developed through training on proteins for which extensive epitope mapping was carried out; generally these datasets were small and the accuracy of the methods unknown. Recently, Blythe and Flower benchmarked the performance of 484 of the propensity scales on a large data set (50 proteins) with extensive epitope mapping and found that even the best methods predict only marginally better than a random prediction (Blythe and Flower, *Protein Sci.* 14:246-248 (2005)).

A number of efforts have attempted to combine various propensity scales to improve predictive power. Alix developed a program called PEOPLE, which predicts the location of linear B-cell epitopes using combinations of propensity scales including secondary structure, hydrophilicity, surface accessibility, and flexibility to generate an "antigenic index" (Alix, *Vaccine* 18:311-314 (1999)). Odorico developed a program, BEPITOPE, for predicting the location of linear B-cell epitopes using a combination of hydrophilicity, accessibility, and turns in proteins propensity scales (Odorico and Pellequer, *J. Mol. Recognit.* 16:20-22 (2003)). Sollner and Mayer developed a machine learning method to predict B-cell epitopes by combining propensity scales, reinterpreting some propensity scales (substituting pair wise difference between adjacent amino acids rather than moving averages), and using residue frequencies such as di and tripeptide occurrences within a local peptide neighborhood (Sollner and Mayer, *J. Mol. Recognit.* 19:200-208 (2006)). The authors claim improvement in performance over other prediction models. Another recent paper reports that a hidden Markov model combined with a hydrophilicity scale improves epitope prediction called BepiPred (Larsen et al., *Immunome Res.* 2:2 (2006). It is not clear at this time how much of an improvement these newer methods actually provide; no study has been done to benchmark the performance of any of these algorithms.

The consensus approach recommended by most commercial entities producing custom polyclonal and monoclonal antibodies is to empirically choose the amino or carboxy termini of the protein of interest as these sequences are more frequently exposed on the exterior of the protein. Indeed many of the commercially available antibodies available for sale are raised against these epitopes. An informal survey of the catalogs of a number of large distributors of antibodies indicates that approximately 40% of all the antibodies for sale are directed at the amino or carboxy termini. The guidance provided by most of these vendors reveals that beyond the empiric amino and carboxy terminal strategies, the recommendation is to use one of the propensity scales introduced more than 20 years ago. Most providers provide "custom" design of epitopes, although this generally uses propensity scales and a limited number of rules of thumb.

There is no body of work or database that indicates how well an antibody generated by a conjugated peptide will perform. The best source of information is the antibody producers themselves, who frequently perform custom antibody synthesis for clients as well as develop specific antibodies for sale as individual reagents. Six large producers of custom antibodies were surveyed, and their responses to queries regarding success rate was generally in agreement, providing the best estimates, summarized as follows. There is a very high success rate in generating a high titer antibody to a conjugated peptide epitope. This is determined by performing an indirect ELISA against the immunizing peptide alone. A number of vendors guarantee such a response, though the "best guess" from those consulted is 90-95% success. Most failures can be addressed by re-conjugation and immunization of a new animal or changing to a different animal type. The experts also generally agree that the range of success for these antibodies in reacting to whole protein in a western blot (where it has been denatured), is approximately 50% with a range from 40 to 60% being quoted. There was much more uncertainty regarding the success of antibodies in assays requiring specificity to native proteins, estimated to be about 30 to 40%. This informal survey highlights one of the deficiencies in the field; no publicly available study defines these parameters with any confidence. In addition, the low numbers associated with the success rate for applications directed at native epitopes means that significant resources are wasted in the process.

It is clear that the state of the art for choosing peptide antigens is unsatisfactory. The deficiencies in this field are made more apparent when taken in the context of the developments of the last decade. Array based platforms interrogating tens of thousands of gene products can generate numerous biological insights that could be tested at the protein level if reagents were available. Proteomic platforms likewise produce hundreds to thousands of observations in the research setting that need follow up studies on clinical specimens. To add to the frustration with the current situation, there have been pathologic platform developments such as tissue microarrays that allow the rapid assessment of hundreds or even thousands of patient samples with antibodies for markers of interest. Unfortunately if no antibody is available for a protein, these platforms are moot. It is also clear that the industry for generating both polyclonal and monoclonal antibodies is mature and ready to handle the demand that would come if generation of a reactive antibody was more certain. There are hundreds of vendors nationally using rabbits, mice and chickens for polyclonal production. Monoclonal production is now possible with mouse, rat, and rabbit B cells; techniques have recently been commercialized to generate monoclonal antibodies through the use of a recombinant retrovirus that constitutively expresses the v-abl and c-myc oncogenes. When used to infect immunized mice, this virus rapidly and efficiently induces plasmacytomas to secrete antigen specific monoclonal antibodies (Huppi et al., *Biotechniques,* 29:1100-1106 (2000); Largaespada et al., *J. Immunol. Methods,* 197:85-95 (1996)).

In the future, antibodies are likely to play a growing role in cancer diagnostics and therapeutics as findings from new high throughput technologies define novel protein targets. The methods of producing antibodies, both polyclonal and monoclonal have reached maturity. Unfortunately, guidance on the choice of a peptide epitope has not changed in over two decades; empiric rules and propensity scales still dominate most prediction schemes. The end result is that at least half of conjugated peptide immunizations produce no antibody capable of reactivity, even in a denaturing immunoblot. When it comes to more demanding tasks such as immunohistochemistry, immunoprecipitation and fluorescence activated cell sorting (FACS), the performance is significantly worse. This represents a tremendous waste of time and resources that demands a better solution. As disclosed herein, proteomics based methods have been developed that identify glycosylation sites on soluble and membrane proteins. Because the carbohydrate groups are hydrophilic and on the protein surface, the methods disclosed herein provide a strategy focused on this protein neighborhood, also referred to herein as the glyprox strategy, that will provide more efficient production of antibodies against glycoproteins than the historical methods.

As disclosed herein, two proteomic strategies have been developed to analyze biological samples based on the selective capture of glycosylated proteins using hydrazide chemistry (Zhang et al., *Nat. Biotechnol.* 21:660-666 (2003)) that improves the effectiveness of generating antibodies to cell surface and secreted proteins. The initial motivation for selecting glycoproteins was two fold: (1) to use this selectivity to reduce the complexity and dynamic range of serum because albumin is lightly glycosylated and (2) to specifically capture proteins destined for the cell membrane and secretion. The methods relate to biomarker identification using a glyco-specific methodology. A method for capturing glycoproteins from solution is described in Example III. Methods for capturing membrane glycoproteins is described in Examples II and IV. Example II details principles of membrane purification using a membrane impermeable bifunctional reagent, biocytin hydrazide. An exemplary protocol for capturing cell surface glycoproteins is described in Example I. It is understood that various modifications of the protocol can be used, as understood by those skilled in the art, can be used so long as sufficient glycoproteins are analyzed, as desired. Studies demonstrating the efficiency of the technique for selective purification of membrane proteins from RAMOS and Jurkat lymphocyte cell lines are described in Example II. The development of a list of T cell overrepresented proteins is given in Example IV. Collectively these results indicate that proteomic analysis can be used as a highly selective method for the identification of biomarkers such as cancer derived biomarkers that will serve as the basis for choosing targets for the generation of antibodies.

In one embodiment, the invention relates to methods for generating antibodies against enzymatically deglycosylated membrane glycopeptides. The methods relate to the generation of antibodies against the enzymatically deglycosylated forms of bona fide cell surface glycopeptides, generally plus and/or minus twenty five amino acid residues from the glycosylation site, depending on antigenicity predictions, that have been previously identified by mass spectrometry. This method is based on the fact that enzymatic deglycosylation of an N-linked glycopeptide with Peptide-N-Glycosidase F (PNGaseF) converts the asparagine residue to its acidic form, aspartic acid. The antibody is raised against a peptide string in which the asparagine residue is deliberately changed to aspartic acid. The newly generated antibody is able to detect a protein target after enzymatic deglycosylation with PNGaseF to unmask the epitope. This technique has wide potential applications including but not limited to western blotting, immunohistochemistry, and cell sorting. Although exemplified with PNGaseF, it is understood that other glycosidases, including N-glycosidases and O-glycosidases that can be used to cleave N-linked and O-linked carbohydrate moieties, respectively.

There are three aspects of this method of the invention. First, using the site of glycosylation indicates that the target peptide sequence is present on the exterior of the protein. Second, raising an antibody to a peptide "mutated" by conversion of asparagine to aspartic acid has a higher likelihood to induce an immune response as it unmasks a typically "invisible" sequence which itself deviates from evolutionarily conserved "self". The invisibility derives from the fact that the attached carbohydrate molecules cause steric hindrance, preventing antibodies access to this residue. Third, aspartic acid is known have greater antigenicity than asparagines. These three features together will significantly increase the likelihood of generating a useful antibody against a protein of interest.

In another embodiment, the invention provides methods for generating antibodies against sequences adjacent to established sites of glycosylation. The method relates to generating antibodies using immunizing sequences based on close proximity to a glycosylation site such as an N-glycosylation site established as an authentic glycosylation site using mass spectrometry. Close proximity is defined as being within twenty-five residues up or downstream of the site of glycosylation. Actual sequence for immunization will be chosen depending on predicted antigenicity. Like the method discussed above, the targets against which the antibodies are raised are known to be on the portion of the protein exterior to the membrane. Also, immunizing peptides will include portions of the sequence identified by mass spectrometry, which means that these residues were not modified post-translationally, and will be accessible to antibodies. Using the mass spectrometry based identification method, the peptides that are identified have unmodified amino acids surrounding the glycosylation site. Any changes in the weight of the amino acid, such as methylation, phosphorylation, or other post-translational modifications, which change the weight of the peptide, will prevent the identification. Thus the observation of a deglycosylated peptide means that all amino acids are unmodified. This also means that this is a good sequence for raising an antibody since, as in the native protein, the amino acids are unmodified. If one uses sequences outside of those identified, there is a risk that there is an unexpected modification on an amino acid which will make it different from the synthetic sequence used for immunization. This portion of identified peptide provides some reassurance that part of the immunizing sequence is just as it is in the native protein.

One of the most significant advantages to this method is that the knowledge of sites of glycosylation provides significant insight into the local structure of the protein. Targeting the region around the glycosylation site dramatically increases the chance that an antibody raised against a peptide epitope will be reactive toward a native protein. This strategy should work especially for generating antibodies for FACS and ELISA assays as well any biopharmaceutical agent, which must be reactive toward native proteins.

Protein glycosylation has long been recognized as a very common post-translational modification. Carbohydrates are linked to serine or threonine residues (O-linked glycosylation) or to asparagine residues (N-linked glycosylation) (Varki et al. *Essentials of Glycobiology* Cold Spring Harbor Laboratory (1999)). Protein glycosylation, and in particular N-linked glycosylation, is prevalent in proteins destined for extracellular environments (Roth, *Chem. Rev.* 102:285-303 (2002)). These include proteins on the extracellular side of the plasma membrane, secreted proteins, and proteins contained in body fluids, for example, blood, serum, plasma, cerebrospinal fluid, urine, breast milk, saliva, lung lavage fluid, pancreatic juice, semen, and the like. These also happen to be the proteins in the human body that are most easily accessible for diagnostic and therapeutic purposes.

Due to the ready accessibility of body fluids exposed to the extracellular surface of cells and the presence of secreted proteins in these fluids, many clinical biomarkers and therapeutic targets are glycoproteins. These include Her2/neu in breast cancer, human chorionic gonadotropin and α-fetoprotein in germ cell tumors, prostate-specific antigen in prostate cancer, and CA125 in ovarian cancer. The Her2/neu receptor is also the target for a successful immunotherapy of breast cancer using the humanized monoclonal antibody HERCEPTIN™ (Trastuzumab) (Shepard et al., *J. Clin. Immunol.* 11:117-127 (1991)). In addition, changes in the extent of glycosylation and the carbohydrate structure of proteins on the cell surface and in body fluids have been shown to correlate with cancer and other disease states, highlighting the clinical importance of this modification as an indicator or effector of pathologic mechanisms (Durand and Seta, *Clin. Chem.* 46:795-805 (2000); Freeze, *Glycobiology* 11:129R-143R (2001); Spiro, *Glycobiology* 12:43R-56R (2002)). Therefore, a method for the systematic and quantitative analysis of glycoproteins would be of significance for the detection of new potential diagnostic markers and therapeutic targets, and the methods of the invention for generation of reagents such as antibodies are particularly useful for generating potential antibody therapeutic agents.

One of the major biosynthetic functions of the endoplasmic reticulum is the covalent addition of sugars to proteins; most of the soluble and membrane-bound proteins that are made in the ER are glycoproteins (Alberts et al., *Molecular Biology of the Cell* New York: Garland Science (2001)). Glycosylation in the ER consists of an en bloc transfer of a preformed precursor oligosaccharide to the side-chain amino group of an asparagine residue in the protein (N-linked). The preformed oligosaccharide is transferred to the target asparagine in a single step immediately after that amino acid translocates into the ER lumen. N-linked glycosylation sites generally fall into the N—X—S/T sequence motif in which X denotes any amino acid except proline (Bause, *Biochem. J.* 209:331-336 (1983)). A second type of glycosylation event in the Golgi links oligosaccharides to the hydroxyl group on the side chain of a serine, threonine, or hydroxylysine, called O-linked glycosylation.

The function of N-linked glycosylation is unknown. It is known that some proteins require N-linked glycosylation for proper folding (Daniels et al., *Mol. Cell*, 11:79-90 (2003); Petrescu et al., *Biochemistry*, 39:5229-5237 (2000)). Two ER chaperone proteins, calnexin and calreticulin, bind to oligosaccharides on incompletely folded proteins and retain them in the ER. Another possible mechanism arises because hydrophilic sugar chains have limited flexibility and protrude from the protein surface. This can thus limit the approach of other macromolecules which tends to make a glycoprotein more resistant to proteolytic attack. Experiments have shown that in some cases, glycosylation is not an absolute requirement for proper folding, but the unglycosylated protein degrades quickly. Finally glycosylation may be involved cell-cell adhesion (Lasky, *Annu. Rev. Biochem.* 64:113-139 (1995)) and molecular recognition (Lis and Sharon, *Chem. Rev.* 98:637-674 (1998)).

A recent large scale analysis was performed characterizing the sites of protein glycosylation using a large crystallographic database including 386 sites of N-linked carbohydrates (Petrescu et al., *Glycobiology*, 14:103-114 (2004)). The sites of glycosylation were characterized as exposed convex surfaces 33%, deep recesses 10% and on the edge of grooves with the glycan filling the cleft 20%. These authors also found an elevated probability of finding glycosylation at sites where secondary structure changes. A third observation was that there were deviations in the expected amino acid composition surrounding the glycosylation sites, particularly an increased occurrence of aromatic residues before the asparagine and threonine. The authors proposed that glycans may play a role in organizing the folding process and that the positions of glycosylation sites may have evolved to act as landmarks for ending or starting regions of regular secondary structure to promote efficient folding. In addition the local hydrophobicity supports the hypothesis that glycans are involved in covering/stabilizing hydrophobic patches of the protein surface (Toyoda et al., *J. Biochem.* 131:511-515 (2002)).

In one embodiment, the invention provides a method for generating an antibody specific for the deglycosylated form of a glycopolypeptide. The method can include the steps of generating a peptide corresponding to an N-linked glycosylation site of a glycopolypeptide, wherein the asparagine corresponding to the N-linked glycosylation site is mutated to an aspartic acid; and generating an antibody having specific binding activity for the peptide, wherein the antibody has specific binding activity for the deglycosylated form of the glycopolypeptide. As disclosed herein, the cleavage of an N-linked glycosylation site with PNGase-F cleaves between the innermost N-acetylglucosamine (GlcNAc) and asparagine residues of high mannose, hybrid and complex oligosaccharides. This cleavage deaminates the asparagine residue to an aspartic acid residue. As used herein, a "mutated" polypeptide sequence refers to a sequence in which one or more amino acid residues are independently substituted with another amino acid, such as aspartic acid for asparagine, relative to a parent sequence, for example, relative to a naturally occurring sequence. By mutating the asparagine glycosylation site to an aspartic acid, the peptide used to generate an antibody against the glycopolypeptide represents the deglycosylated from of the glycopolypeptide. Antibodies generated against such peptides therefore can bind to the deglycosylated form of the glycopolypeptide and can be used, for example, to detect binding to the deglycosylated form.

Generally when making anti-peptide antibodies, it is desirable to use peptides of a minimum size of 6 amino acids (see Harlow and Lane, *Antibodies: A Laboratory Manual*, Cold Spring Harbor Laboratory Press (1988); Doolittle, *Of URFS and ORFS: A Primer on How to Analyze Derived Amino Acid Sequences*, University Science Books, Chapter 5, pp. 63-79 (1986). In one embodiment, the peptide used comprises independently at most 3 amino acids on the amino and carboxyl terminal side of the N-glycosylation site. As used herein, "independently" means that the number of amino acids on the amino or carboxyl terminal side of the N-glycosylation site are independently chosen to be the recited size and do not necessarily have to be the same size on each side of the glycosylation site. For example, a peptide comprising independently at most 3 amino acids on the N-terminal and C-terminal side can be selected with 2 amino acids on the N-terminal side and 3 amino acids on the C-terminal side. Such an exemplary peptide independently comprising at most 3 amino acids on the N-terminal and C-terminal side of the N-glycosylation site would contain 6 amino acids, the aspartic acid at the mutated glycosylation site, 2 N-terminal amino acids and 3 C-terminal amino acids flanking the glycosylation site. Other exemplary peptides independently comprising at most 3 amino acids on the N-terminal and C-terminal side of the N-glycosylation site would be a peptide containing 3 N-terminal amino acids and 2 C-terminal amino acids, or a peptide containing 3 N-terminal amino acids and 3 C-terminal amino acids. In another embodiment, the peptide can comprise independently at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, or at most 30 amino acids on the amino and carboxyl terminal side of the N-glycosylation site. It is understood that longer peptides can be synthesized as desired for a particular use.

In another embodiment of a method for generating an antibody specific for the deglycosylated form of a glycopolypeptide, the method can further comprise identifying the N-linked glycosylation site. For example, an N-linked glycosylation site can be identified by mass spectrometry, as disclosed herein.

The invention additionally provides a method for generating an antibody specific for a glycopolypeptide. The method can include the steps of generating a peptide corresponding to amino acids adjacent to an N-linked glycosylation site of a glycopolypeptide, wherein the N-linked glycosylation site has been identified using mass spectrometry as an authentic glycosylation site; and generating an antibody having specific binding activity for the peptide, wherein the antibody has specific binding activity for the native form of the glycopolypeptide. The native form is the folded form of the polypeptide, that is, non-denatured.

As used herein, an "authentic glycosylation site" refers to a glycosylation site that has been empirically and experimentally determined to be a bona fide glycosylation site. An authentic glycosylation site, having been experimentally determined to be an actual glycosylation site, is distinct from a putative glycosylation site which has not been experimentally determined to be a glycosylation site. As discussed herein, the consensus sequence for N-linked glycosylation is N—X—S/T, and any given protein will generally have a number of such consensus sequences which, if located on a secreted protein or the extracellular domain of a membrane protein, are potential N-linked glycosylation sites. However, it is known that not all such sites are actually glycosylated at the consensus N—X—S/T site, and it has been traditionally difficult to routinely determine which, if any, of such sites are actually glycosylated in a particular cell or tissue. However, as disclosed herein, methods of labeling glycopolypeptides and analysis by mass spectrometry have allowed the identification of authentic glycosylation sites of glycopolypeptides. The generation of antibodies to peptides adjacent to authentic glycosylation sites increases the likelihood that the antibodies will react with native protein since the glycosylation sites are exposed and not buried within the folded glycopolypeptide.

As used herein, the phrase "adjacent to an N-linked glycosylation site" refers to the amino acids proximal to the glycosylation site in the linear sequence. Amino acids adjacent to an N-linked glycosylation site include the amino acids immediately adjacent to the glycosylation site, that is −1 amino acid on the N-terminal side and +1 amino acid on the C-terminal side. An adjacent amino acid can also include within up to a few amino acids N-terminal or C-terminal of the glycosylation site, for example, −2 or +2, −3 or +3, −4 or +4, −5 or +5, and the like, so long as the peptide generated corresponds to amino acids adjacent to an N-linked glycosylation site such that an antibody generated against the peptide has specific binding activity for the native form of the glycopolypeptide.

As discussed above, it is generally desired to use at least a 6 amino acid sequence to generate an anti-peptide antibody. In a method for generating an antibody specific for an authentic N-linked glycosylation site of a glycopolypeptide, the peptide can comprise, for example, at most 6 amino acids on the amino or carboxyl terminal side of the N-glycosylation site. In addition, a peptide can comprise at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, or at most 25 amino acids on the amino or carboxyl terminal side of the N-glycosylation site. Larger peptides having at most 30, 35, 40, or more amino acids can be used, as desired.

In one embodiment of a method of the invention, the glycopolypeptide can been isolated using hydrazide chemistry, for example, using biocytin hydrazide. Exemplary methods for isolating a glycopolypeptide using hydrazide chemistry are described in the Examples.

Methods for identifying authentic glycosylation sites using mass spectrometry are described in the Examples. It is understood that mass spectrometry can be used to identify an authentic glycosylation site. However, when referring to the peptides comprising independently at most a given number of amino acids or to those adjacent to a glycosylation site such as a N-linked glycosylation site, it is understood that it is the site of glycosylation that is identified by mass spectrometry, not necessarily the entire peptide being used in the methods of the invention. For example, mass spectrometry can be used to identify the glycosylation site and, based on the sequence of the peptide analyzed by mass spectrometry, the information can be used to identify the glycoprotein and the glycosylation site (see Example II). The identification of the glycoprotein is determined by comparing the sequence to a database of protein sequences and identifying the protein that corresponds to the peptide analyzed by mass spectrometry. Once the glycoprotein is identified, the known sequence of the glycoprotein, irrespective of the specific peptide analyzed by mass spectrometry to identify the glycosylation site, can be used to select a desired peptide size for use in a method of the invention, as disclosed herein. Although MS methods are particularly useful for identifying authentic glycosylation sites, as disclosed herein, it is understood that other methods to identify an authentic glycosylation site can also be used, as desired.

Methods of mass spectrometry analysis are well known to those skilled in the art (see, for example, Yates, *J. Mass Spect.* 33:1-19 (1998); Kinter and Sherman, *Protein Sequencing and Identification Using Tandem Mass Spectrometry*, John Wiley & Sons, New York (2000); Aebersold and Goodlett, *Chem. Rev.* 101:269-295 (2001)). For high resolution polypeptide fragment separation, liquid chromatography ESI-MS/MS or automated LC-MS/MS, which utilizes capillary reverse phase chromatography as the separation method, can be used (Yates et al., *Methods Mol. Biol.* 112:553-569 (1999)). Data dependent collision-induced dissociation (CID) with dynamic exclusion can also be used as the mass spectrometric method (Goodlett et al., *Anal. Chem.* 72:1112-1118 (2000)).

Methods for synthesizing peptides are well known to those skilled in the art. Methods for peptide synthesis and the production of peptide libraries have been described (see, for example, Merrifield, *Methods Enzymol.* 289:3-13 (1997); Fodor et al., *Science* 251:767 (1991); Gallop et al., *J. Med. Chem.* 37:1233-1251 (1994); Gordon et al., *J. Med. Chem.* 37:1385-1401 (1994)).

Although exemplified herein with N-linked glycosylation, it is understood that methods of the invention can also be used with other types of authentically identified glycosylation sites, such as O-linked glycosylation sites or other identified glycosylation sites, for example, glycosylphosphatidylinisotol (GPI) anchored proteins. For example, peptides adjacent to authentic O-linked or GPI-linked sites can be synthesized and antibodies generated, as described herein.

The invention additionally provide antibodies generated by the methods disclosed herein, for example, antibodies specific for the deglycosylated form of a glycopolypeptide. It is understood that such an antibody binds specifically to the deglycosylated form of a glycopolypeptide but not the glycosylated form. The invention further provides antibodies specific for a peptide corresponding to amino acids adjacent to an authentic N-linked glycosylation site. Methods for preparing antibodies are well known to those skilled in the art. As used herein, the term "antibody" is used in its broadest sense to include polyclonal and monoclonal antibodies, as well as antigen binding fragments of such antibodies. An antibody useful in the invention, or antigen binding fragment of such an antibody, is characterized by having specific binding activity for an antigen or epitope, such as a polypeptide or a peptide portion thereof, of at least about $1 \times 10^5$ M$^{-1}$. Thus, Fab, F(ab')$_2$, Fd, Fv, single chain Fv (scFv) fragments of an antibody and the like, which retain specific binding activity for an antigen or epitope such as a polypeptide, are included within the definition of an antibody. Specific binding activity of an antibody for an antigen or epitope such as a polypeptide can be readily determined by one skilled in the art, for example, by comparing the binding activity of an antibody to a particular antigen or epitope such as a polypeptide versus a control antigen or epitope such as a polypeptide that is not the particular antigen/epitope or polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)). If desired, the peptide antigens used to generate antibodies can be coupled to an appropriate carrier, as desired and described in Harlow and Lane, supra, 1988.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making functional antibodies are well known to those skilled in the art (Winter and Harris, *Immunol. Today* 14:243-246 (1993); Ward et al., *Nature* 341: 544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

The cell surface glycoprotein capture technology disclosed herein allows for specific detection and relative quantification via stable isotope labeling of biologically and potentially medically relevant cell surface marker proteins, including those partitioning into lipid rafts (see, for example, Wollscheid et al., *Subcell. Biochem.* 37:121-152 (2004); Wollscheid et al., *Curr. Opin. Immunol.* 16:337-344 (2004); Desiere et al., *Genome Biol.* 6:R9 (2004)). In contrast to previous approaches, the present method allows the identification of proteins in any one experiment that represent genuine plasma membrane molecules at the time of the cell surface labeling. Thus, the present method allows confirmation and annotation of proteins in publicly available databases as bona fide plasma membrane proteins. Furthermore, the initial results allow the specification of the experimentally verified N-glycosylation site(s) within the identified proteins. For the first time, such technology will allow for the scanning of cell surfaces in a discovery-driven approach. Known as well as hypothetical proteins involved in lipid raft and/or T cell signaling have already been identified, which can be followed up to more precisely determine their biological function.

The present methods allow transfer of the cell surface and glycoprotein labeling strategy to target plasma membrane proteins in primary cells, for example, macrophages, stem cells, and the like, and tissue samples from leukemia (CLL/ ALL) and prostate cancer patients, for example, in collaboration with National Cancer Institute (NCI) and the Fred Hutchinson Cancer Research Center (FHCRC), as well as to other desired cell or tissue samples. The identification of peptides can be transferred to the MALDI platform. Additional glycopolypeptide capture techniques can also be used, for example, magnetic hydrazide microbeads for covalent attachment to cell surface glycoproteins as a alternate enrichment strategy. These beads allow identification not only of N-linked glycopeptides, but also O-linked and GPI-linked peptides/proteins, further increasing coverage of the plasma membrane (PM) subproteome.

Although exemplified herein with a solid phase glycopolypeptide capture technology, for example using biocytin hydrazide, it is understood that other glycopolypeptide capture methods can be used, such as those taught in U.S. Publications 2004/0023306 and 2006/0141528, each of which is incorporated herein be reference. Other methods for identifying glycosylation sites can utilize a solution based strategy that can be used to capture glycoproteins from solution. This solution can be the tissue culture media from cells in culture, blood or other bodily fluids, or lysate of cells (see for example, Zhang et al., Nat. Biotechnol. 21:660-666 (2003), which is incorporated herein by reference. An exemplary method of purifying and identifying glycoproteins from solution is described in Example III. It is thus understood that a variety of methods can be used to identify authentic glycosylation sites, in particular using mass spectrometry.

Thus, the methods of the invention can be used generate antibodies against authentic glycosylation sites of a glycopolypeptide. The methods are particularly useful for generating antibodies to authentic glycosylation sites identified by mass spectrometry. As exemplified herein, the glycosylation sites can be N-linked glycosylation sites, but other authentic glycosylation sites such as O-linked or GPI-linked sites can be used. The methods are particularly useful for generating antibodies against authentic N-linked glycosylation sites. Such N-linked glycosylation sites can be identified, for example, using chemical capture such as biocytin hydrazide or other carbohydrate-specific chemistries, as described herein. Such methods allow for the enrichment for glycopolypeptides that can be subsequently analyzed by mass spectrometry.

Additional studies can be performed using a metabolic labeling strategy in vivo with a modified sugar that gets incorporated into cell surface glycoproteins, similarly allowing for their selective isolation and characterization of glycoproteins. Further, the cell surface glycoprotein labeling strategy can be combined with quantitative proteomics methods, such as those taught in U.S. Publications 2004/0023306 and 2006/0141528. Other methods include using amino-reactive isobaric tags such as iTRAQ™ reagents (Applied Biosystems, Foster City Calif.), which can be employed to simultaneously identify and provide relative quantitation of up to four related protein samples. This can be done to elucidate the role of newly identified key cell surface molecules in follow-up experiments as potential differentiation or bio-markers, using, for example, green fluorescent protein (GFP)-tagging, tandem affinity purification (TAP)-tagging, generation of antibodies, and the like.

The methods can also be used to investigate post-translational modifications in cell surface proteins and lipid rafts, for example, using solid phase technology allowing characterization of protein phosphorylation sites in cell surface and lipid raft co-isolating proteins via LC-MS/MS (see Tao et al., Nat. Methods 2:591-598 (2005)).

The above-described cell surface scanning technology has great potential to cast new light on the membrane and lipid raft proteins involved in signal transduction. A combination of biology, chemistry, proteomics and bioinformatics has proven to be a powerful combination of tools for the identification of new and unknown proteins relevant to the system under study, as well as for the identification of known proteins whose signaling involvement would not likely have been predicted from existing data. With an ability to identify surface proteins at high confidence, this allows for the improved elucidation of differentiation markers for disease and for the identification of better targets for immunotherapy in the case of cancer or other diseases. In addition, the methodologies are widely applicable to most cell systems.

The present methods allow for cell surface scanning in a discovery-driven approach, which was impossible before, to specifically identify cell surface proteins in a multiplexed fashion via MS. The present methods also allow the determination of which proteins are expressed on the cell surface of a given cell. The methods also allow for biomarker discovery, for example, what differentiates a cancer cell from a "normal" cell. The methods additionally allow discovery of general differentiation markers, for example, for developmental stages of cells, lineage commitment of stem cells, and the like. The methods further allow identification of cell surface proteins, and the methods relating to identification of protein N-glycosylation sites allows determination of the orientation of the identified protein within the plasma membrane.

The invention additionally provides a method to generate an antigen-specific antibody such as a peptide-specific antibody, for example, a peptide containing a glycosylation site (see Example V). The method can include the steps of immunizing an animal with an antigen such as a peptide to generate an immune response against the antigen, isolating antibody producing cells from the immunized animal, and screening the isolated antibody producing cells for expression of an antibody against the immunizing antigen. A cell expressing a desired antibody can be isolated, for example, using FACS and used to generate a monoclonal antibody using well known methods. If desired, more than one antigen can be used to immunize the animal. Thus, the invention can be used to immunize with a plurality of antigens such as a plurality of peptide antigens, for example, 2 or more, 3 or more, 4 or more, 5 or more, 6 or more, 7 or more, 8 or more, 9 or more, 10 or more, 15 or more, 20 or more, or even greater, as desired, and isolated antibody producing cells can be screened for expression of one or more, and potentially all of the immunizing antigens. Thus, the methods can be used to efficiently immunize a single animal with multiple antigens and identify appropriate antibody producing cells such at that a plurality of monoclonal antibodies can be efficiently produced against a plurality of antigens with immunization of a single animal (see Example V).

It is understood that modifications which do not substantially affect the activity of the various embodiments of this invention are also provided within the definition of the invention provided herein. Accordingly, the following examples are intended to illustrate but not limit the present invention.

EXAMPLE I

Cell Surface Scanning Protocol

This example describes a protocol for labeling and characterizing cell surface glycopolypeptides.

MATERIALS, REAGENTS AND BUFFERS: Labeling buffer: phosphate buffered saline (PBS) pH6.5, 0.1% fetal bovine serum (FBS), the pH of the buffer is critical; Periodate, 5 g (#20504; Pierce); Biocytin Hydrazide, 25 mg (#90060, Biotium); Hypotonic lysis buffer: 10 mM Tris pH 7.5, 0.5 M $MgCl_2$; 15 ml Dounce Tissue Grinder (Wheaton); Membrane prep buffer: 280 mM sucrose, 50 mM Morpholinoethanesulfonic acid (MES) pH 6, 450 mM NaCl, 10 mM $MgCl_2$; Ultacentrifuge: L8-M Ultra (Beckmann); Beckmann SW41 swing rotor, 6×12 ml tubes; SW41 rotor; 35,000 rpm, relative centfrifugal force (rcof) 151,263; Ultra Clear Centrifuge tubes, 12 ml; (Beckmann #344059; UltraLink immobilized Streptavidin PLUS (Pierce; #53117); Endoproteinase Lys-C, Excision Grade, 5 µg (#324715, Calbiochem); sequencing grade modified Trypsin, 100 µg (#V5113, Promega); RapiGest (Waters); Ammonium bicarbonate (Sigma; St. Louis Mo.); Peptide: N-Glycosidase F (PNGase F)(New England Biolabs).

HARVESTING CELLS: Collect cells (at least $5 \times 10^8$) in a 50 mL Falcon tube and wash 2× with 50 mL of labeling buffer.

PERIODATE STIMULATION: Dissolve 0.021 g Sodium-meta-periodate in 1 mL of Labeling Buffer and add 500 µL of this solution to 40 mL of cell solution (cell pellet suspended in labeling buffer). Rotate cells at room temperature in the dark for 15 min. Then centrifuge cells for 5 min. at 1500 rpm. Discard the supernatant and wash cells 2× in 50 mL labeling buffer to remove residual periodate and to deplete dead cells/fragments.

CELL SURFACE LABELING: Resuspend pellet in a total volume of 11 mL labeling buffer, then dissolve 30 mg of Biocytin hydrazide in 1 mL labeling buffer. Add this to the cell solution. Label cells for 60 min at room temperature on a rotator on slow speed. Bring volume up to 50 mL, invert several times, and spin at 1500 rpm for 5 min. Discard the supernatant and wash cells 2× in 50 mL labeling buffer to remove residual biocytin hydrazide and to deplete dead cells/fragments.

CELL LYSIS/MEMBRANE PREPARATION: Resuspend cells in 12 mL of detergent free, hypotonic lysis buffer. Allow the cells to swell for 10 min on ice before homogenization. Homogenize cells with 30 strokes using a Dounce homogenizer on ice. Transfer lysate to Eppendorf tubes and spin down nuclear debris at ~2500×g at 4° C. for 10 min. Transfer supernatant to a Falcon tube, resuspend nuclear pellets in a total of 10 mL of lysis buffer (take aliquot, 10 µl), and repeat membrane extraction, (take aliquots, 110 µl each), for a total of two combined membrane fractions. Add an equal volume of membrane prep buffer and allow to sit on ice for 10 minutes. Centrifuge these membrane fractions at 35000 rpm for 1 hour at 4° C. Collect the membranes into a single tube using 200 µl of ammonium bicarbonate. Repeat with 100-200 µl to gather residual membranes. Wash fractions with ~200 µl membrane wash buffer (0.025 M $Na_2CO_3$ pH 11) and let sit on ice for 30 minutes. Spin samples at 35,000 rpm for 30 minutes to remove all traces of $Na_2CO_3$. Gather pellet with ammonium bicarbonate. Dissolve in 50 µl of Rapigest™ (10× stock solution). Add 2-3 µl of tris(2-carboxyethyl)phosphine hydrochloride TCEP depending on the amount of membrane collected. Allow membranes to dissolve overnight at 4° C. Sonicate sample for 15 min to obtain a clear solution. (take aliquot, 5 µl).

GLYCOPEPTIDE CAPTURE: Digest membranes for 4-6 hours with 1 µg (or suitable amount) of Lys-C (take aliquot, 5 µl). Use 50 µL of Lys-C and rotate at 37° C. Subsequently, add 20 µg (or suitable amount) of trypsin and digest overnight at 37° C. (take aliquot, 5 µl). Inactivate LysC and trypsin partially by heating the sample to 100° C. for 10 min. Allow the sample to cool down and add 10 µL protease inhibitor cocktail. Spin sample at 14,000 rpm for 10 min. Transfer supernatant into new tube. Discard the pellet, if any. Gather and assemble tubes for capture. Add 1 mL of UltraLink Streptavidin PLUS beads to the column. Spin off any excess liquid after transferring beads to the column and add ammonium bicarbonate to wash. Add digested peptides to column and mix gently by pipetting. Incubate beads with peptides for 1 hour in head over head shaker. Spin beads down. Save flow through for analysis of non-glycosylated peptides (Take aliquot; check for depletion of biotinylated molecules; Dot Blot). Wash beads with at least 10 mL 5M NaCl, followed by 10 mL StimLys buffer 0.5% Triton, followed by 10 mL 5M NaCl, followed by at least 10 mL 1100 mM sodium carbonate pH11, followed by at least 5 mL 100 mM ammonium bicarbonate. Suspend the beads in 600 µL 100 mM ammonium bicarbonate and elute glycoproteins from the beads using 1 µl PNGaseF overnight at 37 C. Spin off ammonium bicarbonate into a fresh 2 mL tube. Repeat by adding additional ammonium bicarbonate and keeping the flow through. This flow through contains the cleaved peptides. Dry down eluates using a SpeedVac and suspend peptides in ~40 µl HPLC Buffer A for LCMS/MS or in a buffer suitable for further separation. Transfer to small eppendorf tube and spin down at max. speed for few minutes to collect any precipitate at the bottom. Repeat as needed. Transfer to tube for MS analysis.

EXAMPLE II

Chemical Tagging and Profiling of Plasma Membrane Glycoproteins by Mass Spectrometry This example describes profiling of plasma membrane glycopolypeptides by chemical tagging and characterization by MS.

A biocytin-hydrazide based purification of membrane proteins is described. Briefly, the purification of extracellular membrane proteins using biocytin-hydrazide uses five basic steps. (1) Gentle oxidation of the sugar molecules present on extracellular glycoproteins with sodium meta-periodate converts the cis-diol groups of carbohydrates to aldehydes. (2) Biocytin hydrazide, which is membrane impermeable, is added atop the live cells to form covalent hydrazone bonds with extracellular glycoproteins. (3) Cells are lysed, and a crude microsomal preparation is made by ultra-centrifugation. (4) Proteins are digested to peptides with trypsin. (5) Modified glycopeptides are captured using streptavidin-agarose. (6) The beads are washed and peptides are released from the resin by enzymatic cleavage with PNGase-F, which cleaves between the innermost GlcNAc and asparagine residues of high mannose, hybrid and complex oligosaccharides. This cleavage deaminates the asparagine residue to an aspartic acid residue, a change that can add specificity to peptide identification. Steps one and two are illustrated in FIG. 1. This method has been developed that permits high efficiency purification of membrane glycopeptides.

New methodologies for the specific labeling of proteins residing in the plasma membrane have been developed. One approach utilizes a three-step tandem affinity labeling strategy to confer this desired specificity for the plasma membrane (PM) (FIG. 2) and lipid raft subproteomes (see Example I). These steps are: i) gentle, covalent chemical labeling of carbohydrate-containing proteins on living cells; ii) specific enzymatic peptide release that allows for systematic and selective identification of N-glycosylated peptides derived from the surface glycoproteins; iii) subsequent peptide and protein identification via reversed phase capillary liquid chromatography coupled to tandem mass spectrometry (LC-MS/MS). Results from model cell lines are yielding a never seen before degree of specificity for the detection of low abundance lipid raft-associated and cell surface molecules, with <10% contamination from intracellular and non-glycosylated peptides/proteins (FIG. 3B). The "contaminations" can be singled out in a bioinformatics approach, yielding 100% bona fide plasma membrane proteins. A second, similar approach is also under investigation, in which cells are metabolically labeled in vivo with a modified sugar that gets incorporated into cell surface glycoproteins, again allowing for their selective isolation and characterization.

Figure 2:
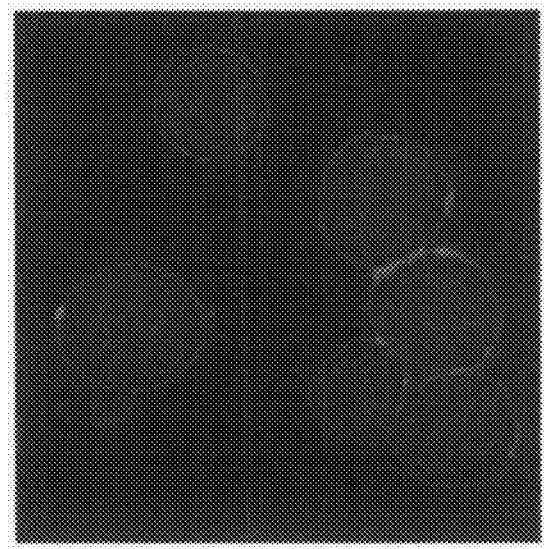
FIG. 2 shows the results of a cell surface labeling technique that is cell surface specific. Shown are Ramos B cells upon visualization of the tagged cell surface proteins, which are subsequently identified via LC-MS/MS (Green: cell surface glycoprotein stain; Blue: Hoechst nuclear stain).

As shown in FIG. 2, the cell surface labeling technology is cell surface specific. Shown are Ramos B cells upon visualization of the tagged cell surface proteins, which are subsequently identified via LC-MS/MS (Green: cell surface glycoprotein stain; Blue: Hoechst nuclear stain).

Figure 3:
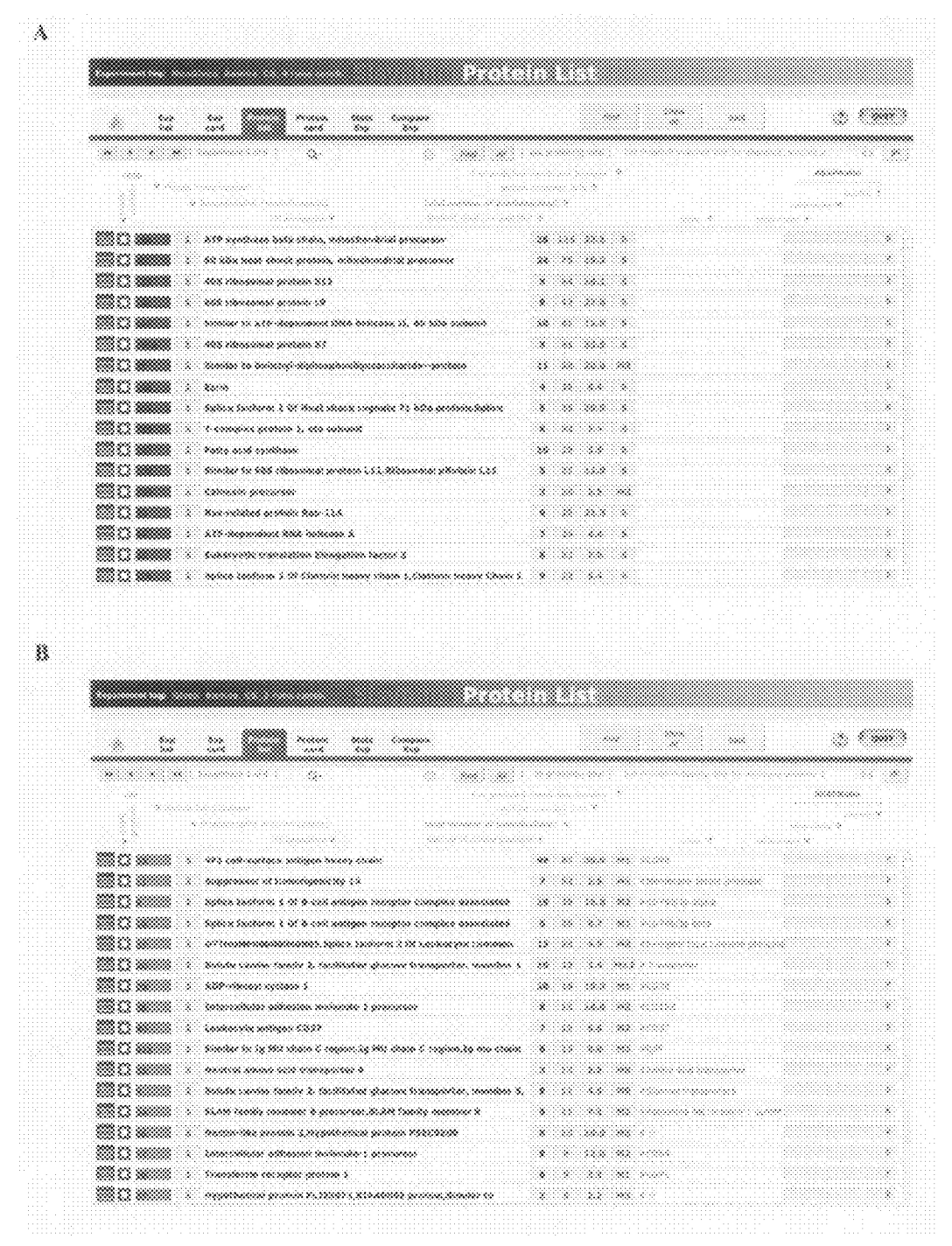

FIG. 3 shows identified proteins of lipid raft co-isolated proteins before and after applying the cell surface glyco-capture technology. FIG. 3A shows identified proteins in a membrane preparation without using the cell surface glyco-capture technology. FIG. 3B shows identified proteins in a membrane preparation using the cell surface glyco-capture technology. Shown in each case is a partial list of protein identifications from a typical LC-MS/MS experiment, sorted according to the total number of identified peptides, with a protein probability of higher than 0.5, as calculated by ProteinProphet™ using statistical analysis (Nesvizhskii et al., *Anal. Chem.* 75:4646-4658 (2003)). The protein probability is an indicator for the likelihood that a particular protein was present in the sample. Displayed columns include the IPI annotation; the number of uniquely identified peptides/protein; the total number of identified peptides/protein. The SOSUI webserver was used to predict transmembrane domains in the retrieved protein sequences (green column; S=soluble; M1=one transmembrane domain, M2=two transmembrane domains, etc.). As shown in FIG. 3A, mostly soluble proteins (green column) were identified compared to FIG. 3B, where only membrane proteins were identified.

Figure 4:
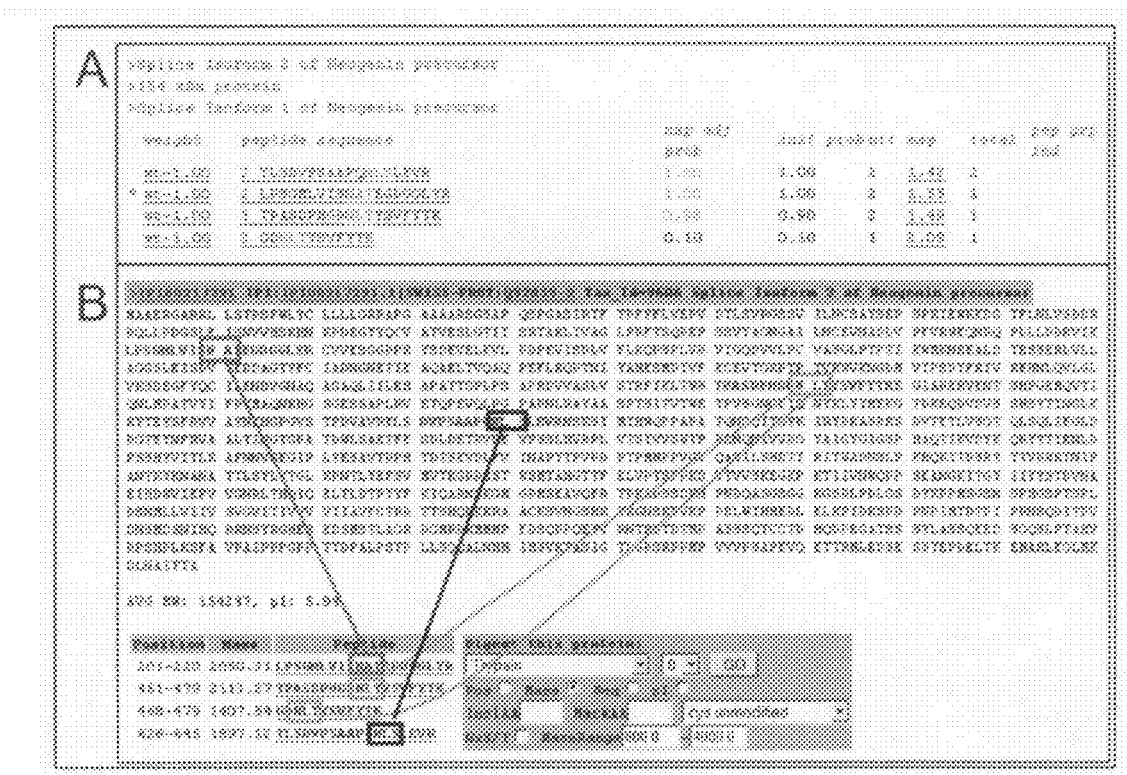
FIG. 4 shows mass spectrometry results for a single glycoprotein. In the upper window. In the upper window (FIG. 4A) all peptides identified for Neogenin are shown (SEQ ID NOS: 38-41). Purple residues mark the location of NXS/T glycosylation motifs. The peptides are shown within the protein sequence below (FIG. 4B) (SEQ ID NOS: 42-46, respectively in order of appearance), with the sites of glycosylation indicated in the colored boxes.

For capture of membrane glycopeptides, a standard "membrane preparation" using hypotonic lysis and differential centrifugation typically produces an impure mixture of microsomes, contaminated with high abundance intracellular cytoplasmic/structural proteins. A proteomic study of such a preparation yields a diverse group of protein identifications with limited specificity for the extracellular membrane. An experiment was performed using RAMOS B lymphocytes, which yielded a typical result. The most abundant proteins from this experiment are not membrane specific, but abundant mitochondrial and ribosomal proteins. Few have membrane spanning domains. A similar study investigating the contents of lipid rafts using differential centrifugation produced similar non-specific results (von Haller et al., *Proteomics*, 1:1010-21 (2001)). In contrast using the present method based on biocytin hydrazide, the proteins found are highly enriched for bona fide membrane proteins as illustrated in FIG. 3B, where it is seen that all of the proteins identified have at least one membrane spanning domain. In developing this method, specific washing steps have been added that significantly reduce the non-specific binding to streptavidin agarose, and typically find that approximately ninety percent of proteins identified are membrane proteins. Additional wash steps can be included, as desired. A typical mass spectrometry result for a single glycoprotein is shown in FIG. 4.

EXAMPLE III

Purification of Glycoproteins from Solution

This example describes the analysis of serum based on the selective extraction of glycosylated proteins using hydrazide resin, followed by digestion with trypsin and elution of only glycopeptides with Peptide-N-Glycosidase F (PNGase-F). This method was also applied to LNCaP cells to improve the specificity for membrane or secreted proteins. This analysis identified 104 unique peptides mapping to 64 unique proteins (1.6 peptides per protein) (Zhang et al., *Nat. Biotechnol.* 21:660-666 (2003)). All the peptides identified contained the conserved N-linked glycosylation motif (N—X—S/T), indicating that formerly N-glycosylated peptides were isolated with high selectivity. Using information from the SWISS-PROT database or the prediction tool PSORT II, 70% were found to be bona fide or predicted transmembrane proteins. The non-transmembrane proteins were mostly designated as either extracellular, 11%, or lysosomal, 14%, thus belonging to two cellular compartments also known to be enriched for glycoproteins.

EXAMPLE IV

Generation of a List of T-lymphocyte Enriched Protein Candidates for Analysis

A current dataset contains approximately 250 membrane proteins from Ramos B cells and about the same number from Jurkat T cells. This list was obtained by pooling the multiple experiments on these cell lines used during method development. The overlap between the B and T cell lines using this method is approximately 35%. This does not mean that proteins seen on one line are not present on the other; expression level for proteins could be low enough that they fall below the limits of detection. A more formal quantitative study is needed to rigorously answer to determine relative protein expression. The list represents an approximation. Table 1 details 35 proteins which will be used as candidates because they are overrepresented on Jurkat T cells. Table 1 lists a sample of 35 proteins (SEQ ID NOS: 1-35) found to be over-represented on Jurkat T cells compared to RAMOS B cells using the surface glycocapture technique. A single peptide sequence containing the site of glycosylation (in bold) is given, though many of these proteins have multiple glycosylation sites identified. The list consists of GPI anchored proteins (indicated with "*"), and proteins with variable numbers of transmembrane domains, indicated in the tm column. The sosui membrane spanning information is also indicated.

TABLE 1

Sample of Proteins Over-represented on Jurkat T Cells Compared to RAMOS B Cells.

| UP symbol | description | peptide sequence | sosui | tm |
|---|---|---|---|---|
| THY1_HUMAN | Thy-1 cell surface antigen variant | HENTSSSPIQYEFSLTR (SEQ ID NO: 1) | M2* | 0 |
| GFRA1_HUMAN | Splice Isoform 1 of GDNF family receptor alpha-1 | ETNFSLASGLEAK (SEQ ID NO: 2) | M1* | 0 |
| CD48_HUMAN | CD48 antigen precursor | ELQNSVLETTLMPHNYSR (SEQ ID NO: 3) | M2* | 1 |
| LFA3_HUMAN | CD 58 Lymphocyte function-associated antigen 3 | VYLDTVSGSLTIYNLTSSDEDEYEMESPNITDTMKM1* (SEQ ID NO: 4) | | 1 |

TABLE 1-continued

Sample of Proteins Over-represented on Jurkat T Cells Compared to RAMOS B Cells.

| UP symbol | description | peptide sequence | sosui | tm |
|---|---|---|---|---|
| IGF1R_HUMAN | Insulin-like growth factor 1 receptor precursor | LILGEEQLEGNYSFYVLDNQNLQQLWDWDHR (SEQ ID NO: 5) | M2 | 1 |
| CD1D_HUMAN | T-cell surface glycoprotein CD1d precursor | TDGLAWLGELQTHSWSNDSDTVR (SEQ ID NO: 6) | M2 | 1 |
| BST2_HUMAN | Bone marrow stromal antigen 2 | NVTHLLQQELTEAQK (SEQ ID NO: 7) | M2 | 1 |
| CD7_HUMAN | T-cell antigen CD7 precursor | DFSGSQDNLTITMHR (SEQ ID NO: 8) | M2 | 1 |
| CD166_HUMAN | CD166 antigen precursor | TVNSLNVSAISIPEHDEADEISDENR (SEQ ID NO: 9) | M2 | 1 |
| MUC18_HUMAN | Isoform 1 of Cell surface glycoprotein MUC 18 | PTISWNVNGTASEQDQDPQR (SEQ ID NO: 10) | M2 | 1 |
| ICAM2_HUMAN | Intercellular adhesion molecule 2 precursor | APQEATATFNSTADR (SEQ ID NO: 11) | M2 | 1 |
| ADA10_HUMAN | ADAM 10 precursor | INTTADEKDPTNPFR (SEQ ID NO: 12) | M2 | 1 |
| CD1C_HUMAN | CD1C antigen, c polypeptide | GNFSNEELSDLELLFR (SEQ ID NO: 13) | M2 | 1 |
| CD69_HUMAN | Early activation antigen CD69 | EFNNWFNVTGSDK (SEQ ID NO: 14) | M1 | 1 |
| O95266_HUMAN | Leukocyte differentiation antigen CD84 isoform | ITQSLMASVNSTCNVTLTCSVEK (SEQ ID NO: 15) | M2 | 1 |
| OXRP_HUMAN | 150 kDa oxygen-regulated protein precursor | VFGSQNLTTVK (SEQ ID NO: 16) | M1 | 1 |
| EMB_HUMAN | Embigin precursor | CQNCFPLNWTWYSSNGSVK (SEQ ID NO: 17) | M1 | 1 |
| EFNB1_HUMAN | Ephrin-B1 precursor | HHDYYITSTSNGSLEGLENR (SEQ ID NO: 18) | M2 | 1 |
| SLAF6_HUMAN | activating NK receptor precursor | NIQVTNHSQLFQNMTCELHLTCSVEDADDNVSFR (SEQ ID NO: 19) | M2 | 1 |
| NEO1_HUMAN | Splice Isoform 1 of Neogenin precursor | VAALTINGTGPATDWLSAETFESDLDETR (SEQ ID NO: 20) | M2 | 1 |
| LYAM1_HUMAN | L-selectin precursor | DNYTDLVAIQNK (SEQ ID NO: 21) | M1 | 1 |
| NICA_HUMAN | Splice Isoform 2 of Nicastrin precursor | DLYEYSWVQGPLHSNETDR (SEQ ID NO: 22) | S | 1 |
| SORT_HUMAN | Sortilin precursor | DITDLINNTFIR (SEQ ID NO: 23) | M2 | 1 |
| CD45_HUMAN | Protein tyrosine phosphatase, receptor type, C | YHLEVEAGNTLVRNESHK (SEQ ID NO: 24) | M2 | 2 |

TABLE 1-continued

Sample of Proteins Over-represented on Jurkat T Cells Compared to RAMOS B Cells.

| UP symbol | description | peptide sequence | sosui | tm |
|---|---|---|---|---|
| PVR1_HUMAN | Poliovirus receptor-related protein 1 precursor | SGQVEVNITEFPYTPSPPEHGR (SEQ ID NO: 25) | M2 | 2 |
| SEM4D_HUMAN | Semaphorin-4D precursor | EAVFAVNALNISEK (SEQ ID NO: 26) | M2 | 2 |
| PTK7_HUMAN | PTK7 protein tyrosine kinase 7 isoform | QDVNITVATVPSWLK (SEQ ID NO: 27) | M2 | 2 |
| CD82_HUMAN | CD82 antigen, Kangai 1 | DYNSSREDSLQDAWDYVQAQVK (SEQ ID NO: 28) | M4 | 4 |
| CD151_HUMAN | CD151 antigen | YHQPGHEAVTSAVDQLQQEFHCCGSNNSQDWR (SEQ ID NO: 29) | M3 | 4 |
| TSN4_HUMAN | Tetraspanin-4 | CCGVSNYTDWFEVYNATR (SEQ ID NO: 30) | M4 | 4 |
| LASS2_HUMAN | LAG1 longevity assurance homolog 2 | LWLPVNLTWADLEDR (SEQ ID NO: 31) | M5 | 5 |
| KCNA3_HUMAN | Potassium voltage-gated channel | DYPASTSQDSFEAAGNSTSGSR (SEQ ID NO: 32) | M5 | 5 |
| LPHN1_HUMAN | Splice Isoform 1 of Latrophilin-1 precursor | DMNATEQVHTATMLLDVLEEGAFLLADNVR (SEQ ID NO: 33) | M8 | 8 |
| GTR1_HUMAN | facilitated glucose transporter member 1 | VIEEFYNQTWVHR (SEQ ID NO: 34) | M12 | 12 |
| CTR1_HUMAN | High-affinity cationic amino acid transporter 1 | NWQLTEEDFGNTSGR (SEQ ID NO: 35) | M14 | 14 |

EXAMPLE V

A Method for High Through-Put Antibody Production Using Glycoprotein Sequences Conjugated to Sulfhydryl and Analyzed by Facs Introduction The ability to identify sensitive and specific diagnostic marker candidates from proteins to monitor health and disease progression is a significant problem in the field of diagnostics. Currently, identification of candidate proteins, development of prototypes (including antibody development) and initial validation of antibodies for diagnostics using standard techniques is slow, requires a recombinant expression system, and purification requires many steps. In some diseases, (i.e., cancer), the specificity of the antibody is tested in different cancer tissues with differing specificity, sensitivity and success. (see Zolg and Langen, *Mol. Cell. Proteomics* 3:345-354 (2004)).

In this example, a high through-put method is described to generate diagnostic marker candidates to develop antibodies against specific epitopes (portion of a molecule to which an antibody binds) to significantly increase specificity, sensitivity and decrease development time. Although polyclonal antibodies can be produced, the ultimate goal is to develop monoclonal antibodies and the methods described herein provide such antibodies. Methods described above will be used to identify and sequence proteins in the native configuration. The protein sequence identified will be used to generate peptides for antibody development. The method is tested in a cancer disease model using the high through-put testing model described.

Materials

Exemplary materials such as Keyhole limpet hemocyanin (KLH) will be supplied as a lyophilized powder, or other suitable form (available, for example, from Cal Bio Chem., La Jolla, Calif.). Alternatively, albumin may be used for conjugation or any other material or substance known in the art may be used. Fluorescein-5-maleimide will be supplied by Pierce (Rockford, Ill.). Alternatively, any other fluorophore known in the art may be used. Peptides to identified protein sequences will be generated by a commercial source such as Sigma-Aldrich (St. Louis Mo.).

Method

Using the methods described herein, protein glycosylation sites will be identified. Sites proximal to these glycosylation sites as described will be chosen for immunization. In one method, specific cysteine residues will be used for labeling. Identified protein sequences that do not have a cysteine residue will have a cysteine residue incorporated at the end of the identified protein sequence to use maleimide labeling, which reacts with the sulfur moiety in cysteine. Maleimide is intended to be exemplary and any other type of labeling known to the skilled artisan is expected to produce the same results. The protein sequence with the added cysteine residue will be used to generate a synthetic peptide using a commercial vendor. The resulting peptide will then be conjugated to keyhole limpet hemocyanin (KLH) as previously described and injected into an animal. KLH is intended to be exemplary. Any other protein (i.e, albumin) that may be used for coupling can be used to produce the desired results. For the proposed method, an exemplary animal is a rabbit, but any suitable animal may be used to produce antibodies. The synthetic peptide will also be coupled to fluorescein-5-maleimide or any other fluorophore known in the art. This exemplary reagent will be used to identify antibody producing cells in the immunized animal. The fluorescein labeled peptide is incubated with a preparation of antibody producing cells from the immunized animal to label only those cells with specific reactivity to the immunizing peptide. Using Fluorescence Activated Cell Sorting (FACS), cells with the fluorescein signal will be identified and only those cells with fluorescein signal will be collected for further testing.

Test Animals

Test animals will be used to generate antibodies. Exemplary test animals include, rabbits, rats or mice or any other animal that would generate an immune response. Animals will be purchased from a certified vendor. Food and water will be provided ad libitum. Test animals will be allowed to acclimate in a temperature and humidity controlled environment for approximately one week prior to the commencement of experimental procedures.

EXAMPLE

Proposed Cancer Diagnostic Markers

In one experiment, the methods described will be used to generate antibodies to ErbB-2, a membrane protein marker used as a diagnostic protein in breast cancer (see: Roskoski, R. Biochem Biophys Res Comm (2004) 319:1-11). This protein has been identified in UniPep (db.systemsbiology.net/sbeams/cgi/Glycopeptide/Glyco_prediction.cgi?action=Show_detail_for m&ipi_data_id=19935) with unique glycosylation sites.

Some of these sites are:

The cell lines reactive to the fluorescein tagged peptides used for immunization are tested for reactivity to ErbB-2 to breast cancer cell lines such as MCF-7, T-47D, SKBR3, MDA-MB-435, and MDA-MB-231 by Western blot, immunohistochemistry and immunoprecipitation of ErbB-2. Each reaction will be quantified and compared to known standards as antibody responses to ErbB-2 are widely known. It is anticipated that Erb B-2 is exemplary and other proteins may serve as useful biomarkers. It is expected that the tagged peptides will produce antibodies to native proteins that will have a statistically greater reactivity when tested by standard immunology methods as the peptides generated will reflect the native protein sequence since they are proximal to a glycosylation site.

Results

The method described herein does not require a recombinant expression system to produce an immunogen, which will decrease the possibility of protein folding and glycosylation, both of which diminish specific antibody responses to the native protein. By identifying proteins based on specific glycosylation sites, the opportunity to produce antibodies to native proteins is enhanced.

An antibody will be developed using peptide immunization based on a predetermined protein sequence that will be specifically identified followed by an antibody response that is monitored by a fluorescent marker that is tagged to the identical protein sequence. The methods described herein are highly specific and designed to sequence a native protein, tag it with fluorescence and identify the antibody response. The method described herein allows immunization of a single animal with multiple peptides simultaneously, with reactivity to be determined after clonal populations are defined, improving the efficiency of the procedure.

This proposed method will significantly decrease the steps of development and will potentially provide greater antibody specificity and significantly decrease development time and costs. In addition, the product generated will be a monoclonal antibody rather than a polyclonal antibody. This is highly desirable when downstream applications include diagnostic

| NXS/T location | Sequence | |
|---|---|---|
| 68 | R.HLYQGCQVVQGNLELTYLPTNASLS.F | (SEQ ID NO: 36) |
| 124 (unknown) | R.GTQLFEDNYALAVLDNGDPLNNTTPVT-GASPGGLR.E | (SEQ ID NO: 37) |

Eight peptides (for each identified glycosylation site) will be generated wherein the cysteine residue is conjugated to KLH. Two rabbits will be injected with unique peptides conjugated to KLH corresponding to 2 glycosylation sites. After the immune response is generated, memory B or plasma cells will be obtained from the animals and will be sorted by FACS for reactivity to one of the fluorescent peptides. Each antibody producing clonal population will be tested using an indirect ELISA assay or surface plasmon resonance to determine the specific peptide against which it is reactive.

or therapeutic assays, because reagent purity and stability of reactivity is essential for any biologic assay or therapeutic reagent.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method to produce an immunizing peptide for generating an antibody specific for a glycopolypeptide, comprising
   (a) isolating a glycosylated portion of said glycopolypeptide by treating said glycopolypeptide with periodate, followed by treating with biocytin hydrazine, and coupling the resultant to streptavidin;
   (b) identifying by mass spectroscopy an amino acid sequence consisting of 6-40 amino acids whose C-terminus or N-terminus is within 5 amino acids upstream or downstream respectively of the N-terminus or C-terminus respectively of a glycosylated site of said glycosylated portion of glycopolypeptide obtained in step (a), wherein said site having the sequence N—X—S/T;
   (c) producing said immunizing peptide corresponding to the amino acid sequence identified in step (b).

2. The method of claim 1 wherein said peptide consists of 6-35 amino acids.

3. The method of claim 1, wherein said peptide consists of 6-30 amino acids.

4. The method of claim 1, wherein said peptide consists of 6-25 amino acids.

5. The method of claim 1, wherein said peptide consists of 6-15 amino acids.

6. The method of claim 1, wherein said peptide consists of 6-10 amino acids.

7. The method of claim 1, wherein said peptide consists of 6-8 amino acids.

8. The method of claim 1, wherein said peptide is further coupled to a heterologous peptide.

9. The method of claim 8, wherein the heterologous peptide is keyhole limpet hemocyanin (KLH).

* * * * *

SEQUENCE LISTING

<160> NUMBER OF SEQ ID NOS: 46

<210> SEQ ID NO 1
<211> LENGTH: 17
<212> TYPE: PRT
<213> ORGANISM: Homo sapiens

<400> SEQUENCE: 1

His Glu Asn Thr Ser Ser Ser Pro Ile Gln Tyr Glu Phe Ser Leu Thr
1               5                   10                  15

Arg

<210> SEQ ID NO 2
<211> LENGTH: 13
<212> TYPE: PRT
<213> ORGANISM: Homo sapiens

<400> SEQUENCE: 2

Glu Thr Asn Phe Ser Leu Ala Ser Gly Leu Glu Ala Lys
1               5                   10

<210> SEQ ID NO 3
<211> LENGTH: 18
<212> TYPE: PRT
<213> ORGANISM: Homo sapiens

<400> SEQUENCE: 3

Glu Leu Gln Asn Ser Val Leu Glu Thr Thr Leu Met Pro His Asn Tyr
1               5                   10                  15

Ser Arg

<210> SEQ ID NO 4
<211> LENGTH: 35
<212> TYPE: PRT
<213> ORGANISM: Homo sapiens

<400> SEQUENCE: 4

Val Tyr Leu Asp Thr Val Ser Gly Ser Leu Thr Ile Tyr Asn Leu Thr
1               5                   10                  15

Ser Ser Asp Glu Asp Glu Tyr Glu Met Glu Ser Pro Asn Ile Thr Asp
                20                  25                  30

Thr Met Lys
            35

<210> SEQ ID NO 5
<211> LENGTH: 31
<212> TYPE: PRT
<213> ORGANISM: Homo sapiens

<400> SEQUENCE: 5

Leu Ile Leu Gly Glu Glu Gln Leu Gly Asn Tyr Ser Phe Tyr Val
1               5                   10                  15

Leu Asp Asn Gln Asn Leu Gln Leu Trp Asp Trp Asp His Arg
                20                  25                  30

<210> SEQ ID NO 6
<211> LENGTH: 23
<212> TYPE: PRT
<213> ORGANISM: Homo sapiens

<400> SEQUENCE: 6

-continued

Thr Asp Gly Leu Ala Trp Leu Gly Glu Leu Gln Thr His Ser Trp Ser
1               5                   10                  15

Asn Asp Ser Asp Thr Val Arg
            20

<210> SEQ ID NO 7
<211> LENGTH: 15
<212> TYPE: PRT
<213> ORGANISM: Homo sapiens

<400> SEQUENCE: 7

Asn Val Thr His Leu Leu Gln Gln Glu Leu Thr Glu Ala Gln Lys
1               5                   10                  15

<210> SEQ ID NO 8
<211> LENGTH: 15
<212> TYPE: PRT
<213> ORGANISM: Homo sapiens

<400> SEQUENCE: 8

Asp Phe Ser Gly Ser Gln Asp Asn Leu Thr Ile Thr Met His Arg
1               5                   10                  15

<210> SEQ ID NO 9
<211> LENGTH: 26
<212> TYPE: PRT
<213> ORGANISM: Homo sapiens

<400> SEQUENCE: 9

Thr Val Asn Ser Leu Asn Val Ser Ala Ile Ser Ile Pro Glu His Asp
1               5                   10                  15

Glu Ala Asp Glu Ile Ser Asp Glu Asn Arg
            20                  25

<210> SEQ ID NO 10
<211> LENGTH: 20
<212> TYPE: PRT
<213> ORGANISM: Homo sapiens

<400> SEQUENCE: 10

Pro Thr Ile Ser Trp Asn Val Asn Gly Thr Ala Ser Glu Gln Asp Gln
1               5                   10                  15

Asp Pro Gln Arg
            20

<210> SEQ ID NO 11
<211> LENGTH: 15
<212> TYPE: PRT
<213> ORGANISM: Homo sapiens

<400> SEQUENCE: 11

Ala Pro Gln Glu Ala Thr Ala Thr Phe Asn Ser Thr Ala Asp Arg
1               5                   10                  15

<210> SEQ ID NO 12
<211> LENGTH: 15
<212> TYPE: PRT
<213> ORGANISM: Homo sapiens

<400> SEQUENCE: 12

Ile Asn Thr Thr Ala Asp Glu Lys Asp Pro Thr Asn Pro Phe Arg
1               5                   10                  15

```
<210> SEQ ID NO 13
<211> LENGTH: 16
<212> TYPE: PRT
<213> ORGANISM: Homo sapiens

<400> SEQUENCE: 13

Gly Asn Phe Ser Asn Glu Glu Leu Ser Asp Leu Glu Leu Leu Phe Arg
1               5                   10                  15

<210> SEQ ID NO 14
<211> LENGTH: 13
<212> TYPE: PRT
<213> ORGANISM: Homo sapiens

<400> SEQUENCE: 14

Glu Phe Asn Asn Trp Phe Asn Val Thr Gly Ser Asp Lys
1               5                   10

<210> SEQ ID NO 15
<211> LENGTH: 23
<212> TYPE: PRT
<213> ORGANISM: Homo sapiens

<400> SEQUENCE: 15

Ile Thr Gln Ser Leu Met Ala Ser Val Asn Ser Thr Cys Asn Val Thr
1               5                   10                  15

Leu Thr Cys Ser Val Glu Lys
                20

<210> SEQ ID NO 16
<211> LENGTH: 11
<212> TYPE: PRT
<213> ORGANISM: Homo sapiens

<400> SEQUENCE: 16

Val Phe Gly Ser Gln Asn Leu Thr Thr Val Lys
1               5                   10

<210> SEQ ID NO 17
<211> LENGTH: 19
<212> TYPE: PRT
<213> ORGANISM: Homo sapiens

<400> SEQUENCE: 17

Cys Gln Asn Cys Phe Pro Leu Asn Trp Thr Trp Tyr Ser Ser Asn Gly
1               5                   10                  15

Ser Val Lys

<210> SEQ ID NO 18
<211> LENGTH: 20
<212> TYPE: PRT
<213> ORGANISM: Homo sapiens

<400> SEQUENCE: 18

His His Asp Tyr Tyr Ile Thr Ser Thr Ser Asn Gly Ser Leu Glu Gly
1               5                   10                  15

Leu Glu Asn Arg
            20

<210> SEQ ID NO 19
<211> LENGTH: 34
<212> TYPE: PRT
<213> ORGANISM: Homo sapiens
```

<400> SEQUENCE: 19

Asn Ile Gln Val Thr Asn His Ser Gln Leu Phe Gln Asn Met Thr Cys
1               5                   10                  15

Glu Leu His Leu Thr Cys Ser Val Glu Asp Ala Asp Asp Asn Val Ser
            20                  25                  30

Phe Arg

<210> SEQ ID NO 20
<211> LENGTH: 29
<212> TYPE: PRT
<213> ORGANISM: Homo sapiens

<400> SEQUENCE: 20

Val Ala Ala Leu Thr Ile Asn Gly Thr Gly Pro Ala Thr Asp Trp Leu
1               5                   10                  15

Ser Ala Glu Thr Phe Glu Ser Asp Leu Asp Glu Thr Arg
            20                  25

<210> SEQ ID NO 21
<211> LENGTH: 12
<212> TYPE: PRT
<213> ORGANISM: Homo sapiens

<400> SEQUENCE: 21

Asp Asn Tyr Thr Asp Leu Val Ala Ile Gln Asn Lys
1               5                   10

<210> SEQ ID NO 22
<211> LENGTH: 19
<212> TYPE: PRT
<213> ORGANISM: Homo sapiens

<400> SEQUENCE: 22

Asp Leu Tyr Glu Tyr Ser Trp Val Gln Gly Pro Leu His Ser Asn Glu
1               5                   10                  15

Thr Asp Arg

<210> SEQ ID NO 23
<211> LENGTH: 12
<212> TYPE: PRT
<213> ORGANISM: Homo sapiens

<400> SEQUENCE: 23

Asp Ile Thr Asp Leu Ile Asn Asn Thr Phe Ile Arg
1               5                   10

<210> SEQ ID NO 24
<211> LENGTH: 18
<212> TYPE: PRT
<213> ORGANISM: Homo sapiens

<400> SEQUENCE: 24

Tyr His Leu Glu Val Glu Ala Gly Asn Thr Leu Val Arg Asn Glu Ser
1               5                   10                  15

His Lys

<210> SEQ ID NO 25
<211> LENGTH: 22
<212> TYPE: PRT
<213> ORGANISM: Homo sapiens

```
<400> SEQUENCE: 25

Ser Gly Gln Val Glu Val Asn Ile Thr Glu Phe Pro Tyr Thr Pro Ser
1               5                   10                  15

Pro Pro Glu His Gly Arg
            20

<210> SEQ ID NO 26
<211> LENGTH: 14
<212> TYPE: PRT
<213> ORGANISM: Homo sapiens

<400> SEQUENCE: 26

Glu Ala Val Phe Ala Val Asn Ala Leu Asn Ile Ser Glu Lys
1               5                   10

<210> SEQ ID NO 27
<211> LENGTH: 15
<212> TYPE: PRT
<213> ORGANISM: Homo sapiens

<400> SEQUENCE: 27

Gln Asp Val Asn Ile Thr Val Ala Thr Val Pro Ser Trp Leu Lys
1               5                   10                  15

<210> SEQ ID NO 28
<211> LENGTH: 22
<212> TYPE: PRT
<213> ORGANISM: Homo sapiens

<400> SEQUENCE: 28

Asp Tyr Asn Ser Ser Arg Glu Asp Ser Leu Gln Asp Ala Trp Asp Tyr
1               5                   10                  15

Val Gln Ala Gln Val Lys
            20

<210> SEQ ID NO 29
<211> LENGTH: 32
<212> TYPE: PRT
<213> ORGANISM: Homo sapiens

<400> SEQUENCE: 29

Tyr His Gln Pro Gly His Glu Ala Val Thr Ser Ala Val Asp Gln Leu
1               5                   10                  15

Gln Gln Glu Phe His Cys Cys Gly Ser Asn Asn Ser Gly Asp Trp Arg
            20                  25                  30

<210> SEQ ID NO 30
<211> LENGTH: 18
<212> TYPE: PRT
<213> ORGANISM: Homo sapiens

<400> SEQUENCE: 30

Cys Cys Gly Val Ser Asn Tyr Thr Asp Trp Phe Glu Val Tyr Asn Ala
1               5                   10                  15

Thr Arg

<210> SEQ ID NO 31
<211> LENGTH: 15
<212> TYPE: PRT
<213> ORGANISM: Homo sapiens

<400> SEQUENCE: 31
```

```
Leu Trp Leu Pro Val Asn Leu Thr Trp Ala Asp Leu Glu Asp Arg
1               5                   10                  15
```

<210> SEQ ID NO 32
<211> LENGTH: 22
<212> TYPE: PRT
<213> ORGANISM: Homo sapiens

<400> SEQUENCE: 32

```
Asp Tyr Pro Ala Ser Thr Ser Gln Asp Ser Phe Glu Ala Ala Gly Asn
1               5                   10                  15

Ser Thr Ser Gly Ser Arg
            20
```

<210> SEQ ID NO 33
<211> LENGTH: 30
<212> TYPE: PRT
<213> ORGANISM: Homo sapiens

<400> SEQUENCE: 33

```
Asp Met Asn Ala Thr Glu Gln Val His Thr Ala Thr Met Leu Leu Asp
1               5                   10                  15

Val Leu Glu Glu Gly Ala Phe Leu Leu Ala Asp Asn Val Arg
            20                  25                  30
```

<210> SEQ ID NO 34
<211> LENGTH: 13
<212> TYPE: PRT
<213> ORGANISM: Homo sapiens

<400> SEQUENCE: 34

```
Val Ile Glu Glu Phe Tyr Asn Gln Thr Trp Val His Arg
1               5                   10
```

<210> SEQ ID NO 35
<211> LENGTH: 15
<212> TYPE: PRT
<213> ORGANISM: Homo sapiens

<400> SEQUENCE: 35

```
Asn Trp Gln Leu Thr Glu Glu Asp Phe Gly Asn Thr Ser Gly Arg
1               5                   10                  15
```

<210> SEQ ID NO 36
<211> LENGTH: 27
<212> TYPE: PRT
<213> ORGANISM: Homo sapiens

<400> SEQUENCE: 36

```
Arg His Leu Tyr Gln Gly Cys Gln Val Val Gln Gly Asn Leu Glu Leu
1               5                   10                  15

Thr Tyr Leu Pro Thr Asn Ala Ser Leu Ser Phe
            20                  25
```

<210> SEQ ID NO 37
<211> LENGTH: 37
<212> TYPE: PRT
<213> ORGANISM: Homo sapiens

<400> SEQUENCE: 37

```
Arg Gly Thr Gln Leu Phe Glu Asp Asn Tyr Ala Leu Ala Val Leu Asp
1               5                   10                  15

Asn Gly Asp Pro Leu Asn Asn Thr Thr Pro Val Thr Gly Ala Ser Pro
```

```
                    20                  25                  30

Gly Gly Leu Arg Glu
        35

<210> SEQ ID NO 38
<211> LENGTH: 18
<212> TYPE: PRT
<213> ORGANISM: Homo sapiens

<400> SEQUENCE: 38

Thr Leu Ser Asp Val Pro Ser Ala Ala Pro Gln Asn Leu Ser Leu Glu
1               5                   10                  15

Val Arg

<210> SEQ ID NO 39
<211> LENGTH: 20
<212> TYPE: PRT
<213> ORGANISM: Homo sapiens

<400> SEQUENCE: 39

Leu Pro Ser Gly Met Leu Val Ile Ser Asn Ala Thr Glu Gly Asp Gly
1               5                   10                  15

Gly Leu Tyr Arg
            20

<210> SEQ ID NO 40
<211> LENGTH: 19
<212> TYPE: PRT
<213> ORGANISM: Homo sapiens

<400> SEQUENCE: 40

Thr Pro Ala Ser Asp Pro His Gly Asp Asn Leu Thr Tyr Ser Val Phe
1               5                   10                  15

Tyr Thr Lys

<210> SEQ ID NO 41
<211> LENGTH: 12
<212> TYPE: PRT
<213> ORGANISM: Homo sapiens

<400> SEQUENCE: 41

Gly Asp Asn Leu Thr Tyr Ser Val Phe Tyr Thr Lys
1               5                   10

<210> SEQ ID NO 42
<211> LENGTH: 1408
<212> TYPE: PRT
<213> ORGANISM: Homo sapiens

<400> SEQUENCE: 42

Met Ala Ala Glu Arg Gly Ala Arg Arg Leu Leu Ser Thr Pro Ser Phe
1               5                   10                  15

Trp Leu Tyr Cys Leu Leu Leu Leu Gly Arg Arg Ala Pro Gly Ala Ala
            20                  25                  30

Ala Ala Arg Ser Gly Ser Ala Pro Gln Ser Pro Gly Ala Ser Ile Arg
        35                  40                  45

Thr Phe Thr Pro Phe Tyr Phe Leu Val Glu Pro Val Asp Thr Leu Ser
    50                  55                  60

Val Arg Gly Ser Ser Val Ile Leu Asn Cys Ser Ala Tyr Ser Glu Pro
65                  70                  75                  80
```

```
Ser Pro Lys Ile Glu Trp Lys Lys Asp Gly Thr Phe Leu Asn Leu Val
            85                  90                  95

Ser Asp Asp Arg Arg Gln Leu Leu Pro Asp Gly Ser Leu Phe Ile Ser
                100                 105                 110

Asn Val Val His Ser Lys His Asn Lys Pro Asp Glu Gly Tyr Tyr Gln
            115                 120                 125

Cys Val Ala Thr Val Glu Ser Leu Gly Thr Ile Ile Ser Arg Thr Ala
130                 135                 140

Lys Leu Ile Val Ala Gly Leu Pro Arg Phe Thr Ser Gln Pro Glu Pro
145                 150                 155                 160

Ser Ser Val Tyr Ala Gly Asn Gly Ala Ile Leu Asn Cys Glu Val Asn
                165                 170                 175

Ala Asp Leu Val Pro Phe Val Arg Trp Glu Gln Asn Arg Gln Pro Leu
            180                 185                 190

Leu Leu Asp Asp Arg Val Ile Lys Leu Pro Ser Gly Met Leu Val Ile
            195                 200                 205

Ser Asn Ala Thr Glu Gly Asp Gly Gly Leu Tyr Arg Cys Val Val Glu
210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Val Leu Pro Cys Val Ala
                260                 265                 270

Ser Gly Leu Pro Thr Pro Thr Ile Lys Trp Met Lys Asn Glu Glu Ala
            275                 280                 285

Leu Asp Thr Glu Ser Ser Glu Arg Leu Val Leu Leu Ala Gly Gly Ser
            290                 295                 300

Leu Glu Ile Ser Asp Val Thr Glu Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
            340                 345                 350

His Glu Ser Met Asp Ile Val Phe Glu Cys Glu Val Thr Gly Lys Pro
            355                 360                 365

Thr Pro Thr Val Lys Trp Val Lys Asn Gly Asp Met Val Ile Pro Ser
370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
            420                 425                 430

Ala Thr Thr Gly Pro Leu Pro Ser Ala Pro Arg Asp Val Val Ala Ser
            435                 440                 445

Leu Val Ser Thr Arg Phe Ile Lys Leu Thr Trp Arg Thr Pro Ala Ser
            450                 455                 460

Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
                485                 490                 495

Gln Val Thr Ile Gln Asn Leu Met Pro Ala Thr Val Tyr Ile Phe Arg
```

-continued

```
            500                 505                 510
Val Met Ala Gln Asn Lys His Gly Ser Gly Glu Ser Ser Ala Pro Leu
        515                 520                 525

Arg Val Glu Thr Gln Pro Glu Val Gln Leu Pro Gly Pro Ala Pro Asn
        530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
                565                 570                 575

Met Glu Lys Gly Thr Asp Lys Glu Gln Asp Val Asp Val Ser Ser His
        580                 585                 590

Ser Tyr Thr Ile Asn Gly Leu Lys Lys Tyr Thr Glu Tyr Ser Phe Arg
        595                 600                 605

Val Val Ala Tyr Asn Lys His Gly Pro Gly Val Ser Thr Pro Asp Val
        610                 615                 620

Ala Val Arg Thr Leu Ser Asp Val Pro Ser Ala Ala Pro Gln Asn Leu
625                 630                 635                 640

Ser Leu Glu Val Arg Asn Ser Lys Ser Ile Met Ile His Trp Gln Pro
                645                 650                 655

Pro Ala Pro Ala Thr Gln Asn Gly Gln Ile Thr Gly Tyr Lys Ile Arg
        660                 665                 670

Tyr Arg Lys Ala Ser Arg Lys Ser Asp Val Thr Glu Thr Leu Val Ser
        675                 680                 685

Gly Thr Gln Leu Ser Gln Leu Ile Glu Gly Leu Asp Arg Gly Thr Glu
        690                 695                 700

Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
                725                 730                 735

Arg Val Pro Glu Val Pro Ser Ser Leu His Val Arg Pro Leu Val Thr
        740                 745                 750

Ser Ile Val Val Ser Trp Thr Pro Pro Glu Asn Gln Asn Ile Val Val
        755                 760                 765

Arg Gly Tyr Ala Ile Gly Tyr Gly Ile Gly Ser Pro His Ala Gln Thr
        770                 775                 780

Ile Lys Val Asp Tyr Lys Gln Arg Tyr Tyr Thr Ile Glu Asn Leu Asp
785                 790                 795                 800

Pro Ser Ser His Tyr Val Ile Thr Leu Lys Ala Phe Asn Asn Val Gly
                805                 810                 815

Glu Gly Ile Pro Leu Tyr Glu Ser Ala Val Thr Arg Pro His Thr Asp
        820                 825                 830

Thr Ser Glu Val Asp Leu Phe Val Ile Asn Ala Pro Tyr Thr Pro Val
        835                 840                 845

Pro Asp Pro Thr Pro Met Met Pro Pro Val Gly Val Gln Ala Ser Ile
        850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
                885                 890                 895

Thr Asn Ile Pro Ala Asn Thr Lys Tyr Lys Asn Ala Asn Ala Thr Thr
        900                 905                 910

Leu Ser Tyr Leu Val Thr Gly Leu Lys Pro Asn Thr Leu Tyr Glu Phe
        915                 920                 925
```

-continued

```
Ser Val Met Val Thr Lys Gly Arg Arg Ser Thr Trp Ser Met Thr
    930                 935                 940

Ala His Gly Thr Thr Phe Glu Leu Val Pro Thr Ser Pro Pro Lys Asp
945                 950                 955                 960

Val Thr Val Val Ser Lys Glu Gly Lys Pro Lys Thr Ile Ile Val Asn
                965                 970                 975

Trp Gln Pro Pro Ser Glu Ala Asn Gly Lys Ile Thr Gly Tyr Ile Ile
            980                 985                 990

Tyr Tyr Ser Thr Asp Val Asn Ala  Glu Ile His Asp Trp  Val Ile Glu
        995                 1000                 1005

Pro Val  Val Gly Asn Arg Leu  Thr His Gln Ile Gln  Glu Leu Thr
    1010                 1015                 1020

Leu Asp  Thr Pro Tyr Tyr Phe  Lys Ile Gln Ala Arg  Asn Ser Lys
    1025                 1030                 1035

Gly Met  Gly Pro Met Ser Glu  Ala Val Gln Phe Arg  Thr Pro Lys
    1040                 1045                 1050

Ala Asp  Ser Ser Asp Lys Met  Pro Asn Asp Gln Ala  Ser Gly Ser
    1055                 1060                 1065

Gly Gly  Lys Gly Ser Arg Leu  Pro Asp Leu Gly Ser  Asp Tyr Lys
    1070                 1075                 1080

Pro Pro  Met Ser Gly Ser Asn  Ser Pro His Gly Ser  Pro Thr Ser
    1085                 1090                 1095

Pro Leu  Asp Ser Asn Met Leu  Leu Val Ile Ile Val  Ser Val Gly
    1100                 1105                 1110

Val Ile  Thr Ile Val Val Val  Val Ile Ile Ala Val  Phe Cys Thr
    1115                 1120                 1125

Arg Arg  Thr Thr Ser His Gln  Lys Lys Lys Arg Ala  Ala Cys Lys
    1130                 1135                 1140

Ser Val  Asn Gly Ser His Lys  Tyr Lys Gly Asn Ser  Lys Asp Val
    1145                 1150                 1155

Lys Pro  Pro Asp Leu Trp Ile  His His Glu Arg Leu  Glu Leu Lys
    1160                 1165                 1170

Pro Ile  Asp Lys Ser Pro Asp  Pro Asn Pro Ile Met  Thr Asp Thr
    1175                 1180                 1185

Pro Ile  Pro Arg Asn Ser Gln  Asp Ile Thr Pro Val  Asp Asn Ser
    1190                 1195                 1200

Met Asp  Ser Asn Ile His Gln  Arg Arg Asn Ser Tyr  Arg Gly His
    1205                 1210                 1215

Glu Ser  Glu Asp Ser Met Ser  Thr Leu Ala Gly Arg  Arg Gly Met
    1220                 1225                 1230

Arg Pro  Lys Met Met Met Pro  Phe Asp Ser Gln Pro  Pro Gln Glu
    1235                 1240                 1245

Ser Val  Arg Asn Thr Pro Ser  Thr Asp Thr Met Pro  Ala Ser Ser
    1250                 1255                 1260

Ser Gln  Thr Cys Cys Thr Asp  His Gln Asp Pro Glu  Gly Ala Thr
    1265                 1270                 1275

Ser Ser  Ser Tyr Leu Ala Ser  Ser Gln Glu Glu Asp  Ser Gly Gln
    1280                 1285                 1290

Ser Leu  Pro Thr Ala His Val  Arg Pro Ser His Pro  Leu Lys Ser
    1295                 1300                 1305

Phe Ala  Val Pro Ala Ile Pro  Pro Pro Gly Pro Pro  Thr Tyr Asp
    1310                 1315                 1320
```

```
Pro Ala Leu Pro Ser Thr Pro Leu Leu Ser Gln Gln Ala Leu Asn
    1325                1330                1335

His His Ile His Ser Val Lys Thr Ala Ser Ile Gly Thr Leu Gly
    1340                1345                1350

Arg Ser Arg Pro Pro Met Pro Val Val Val Pro Ser Ala Pro Glu
    1355                1360                1365

Val Gln Glu Thr Thr Arg Met Leu Glu Asp Ser Glu Ser Ser Tyr
    1370                1375                1380

Glu Pro Asp Glu Leu Thr Lys Glu Met Ala His Leu Glu Gly Leu
    1385                1390                1395

Met Lys Asp Leu Asn Ala Ile Thr Thr Ala
    1400                1405

<210> SEQ ID NO 43
<211> LENGTH: 20
<212> TYPE: PRT
<213> ORGANISM: Homo sapiens

<400> SEQUENCE: 43

Leu Pro Ser Gly Met Leu Val Ile Ser Asn Ala Thr Glu Gly Asp Gly
1               5                   10                  15

Gly Leu Tyr Arg
            20

<210> SEQ ID NO 44
<211> LENGTH: 19
<212> TYPE: PRT
<213> ORGANISM: Homo sapiens

<400> SEQUENCE: 44

Thr Pro Ala Ser Asp Pro His Gly Asp Asn Leu Thr Tyr Ser Val Phe
1               5                   10                  15

Tyr Thr Lys

<210> SEQ ID NO 45
<211> LENGTH: 12
<212> TYPE: PRT
<213> ORGANISM: Homo sapiens

<400> SEQUENCE: 45

Gly Asp Asn Leu Thr Tyr Ser Val Phe Tyr Thr Lys
1               5                   10

<210> SEQ ID NO 46
<211> LENGTH: 18
<212> TYPE: PRT
<213> ORGANISM: Homo sapiens

<400> SEQUENCE: 46

Thr Leu Ser Asp Val Pro Ser Ala Ala Pro Gln Asn Leu Ser Leu Glu
1               5                   10                  15

Val Arg
```